(12) United States Patent
Shusterman

(10) Patent No.: US 11,253,159 B2
(45) Date of Patent: Feb. 22, 2022

(54) TRACKING CARDIAC FORCES AND ARTERIAL BLOOD PRESSURE USING ACCELEROMETERS

(71) Applicant: Vladimir Shusterman, Pittsburgh, PA (US)

(72) Inventor: Vladimir Shusterman, Pittsburgh, PA (US)

( * ) Notice: Subject to any disclaimer, the term of this patent is extended or adjusted under 35 U.S.C. 154(b) by 1211 days.

(21) Appl. No.: 15/693,141

(22) Filed: Aug. 31, 2017

(65) Prior Publication Data

US 2018/0020931 A1 Jan. 25, 2018

Related U.S. Application Data

(63) Continuation-in-part of application No. 14/196,738, filed on Mar. 4, 2014, now Pat. No. 9,801,607, which is a continuation-in-part of application No. 13/017,043, filed on Jan. 30, 2011, now Pat. No. 8,706,464.

(60) Provisional application No. 62/442,371, filed on Jan. 4, 2017, provisional application No. 61/300,004, filed on Jan. 31, 2010.

(51) Int. Cl.

| | |
|---|---|
| *A61B 5/0205* | (2006.01) |
| *A61N 1/362* | (2006.01) |
| *A61B 5/11* | (2006.01) |
| *A61B 5/021* | (2006.01) |
| *A61B 8/04* | (2006.01) |
| *A61B 5/02* | (2006.01) |
| *A61B 5/00* | (2006.01) |
| *A61B 5/08* | (2006.01) |
| *A61B 5/029* | (2006.01) |
| *A61B 5/0533* | (2021.01) |
| *A61B 5/024* | (2006.01) |
| *A61B 8/00* | (2006.01) |
| *A61B 5/318* | (2021.01) |
| *A61B 5/352* | (2021.01) |
| *A61B 5/389* | (2021.01) |

(52) U.S. Cl.
CPC ...... *A61B 5/02055* (2013.01); *A61B 5/02007* (2013.01); *A61B 5/02116* (2013.01); *A61B 5/02125* (2013.01); *A61B 5/1102* (2013.01); *A61B 8/04* (2013.01); *A61N 1/3627* (2013.01); *A61B 5/021* (2013.01); *A61B 5/024* (2013.01); *A61B 5/029* (2013.01); *A61B 5/02014* (2013.01); *A61B 5/0533* (2013.01); *A61B 5/0826* (2013.01); *A61B 5/318* (2021.01); *A61B 5/352* (2021.01); *A61B 5/389* (2021.01); *A61B 5/4818* (2013.01); *A61B 5/4848* (2013.01); *A61B 5/4884* (2013.01); *A61B 5/6805* (2013.01); *A61B 5/6833* (2013.01); *A61B 5/7275* (2013.01); *A61B 8/4236* (2013.01); *A61B 2560/0443* (2013.01); *A61B 2562/0219* (2013.01); *A61B 2562/164* (2013.01)

(58) Field of Classification Search
CPC ............ A61B 5/02055; A61B 5/02007; A61B 5/02116; A61B 5/02125; A61B 5/1102; A61B 8/04; A61N 1/3627
USPC .......................................................... 702/19
See application file for complete search history.

(56) References Cited

U.S. PATENT DOCUMENTS 10,413,475 B2 * 9/2019 Centen ................... G16H 40/63

* cited by examiner

*Primary Examiner* — Jerry Lin

(57) ABSTRACT

Modular, miniaturized cardiovascular sensors, systems, methods, and wearable devices for the non-obtrusive evaluation, monitoring, and high-fidelity mapping of cardiac mechanical and electromechanical forces and central arterial blood pressure are presented herein. The sensor manufacturing process is also presented. Using accelerometers, the sensors register body-surface (preferably torso-surface) movements and vibrations generated by cardiac forces. The sensors may contain single-use or reusable components, which may be exchanged to fit different body sizes, shapes, and anatomical locations; they may be incorporated into clothing, bands, straps, and other wearable arrangements. The invention presents a practical, noninvasive solution for electromechanical mapping of the heart, which is useful for a wide range of healthcare applications, including the remote monitoring of heart failure status and the guidance of cardiac resynchronization therapy. Exercise and cardiovascular fitness tracking applications are also presented.

28 Claims, 24 Drawing Sheets

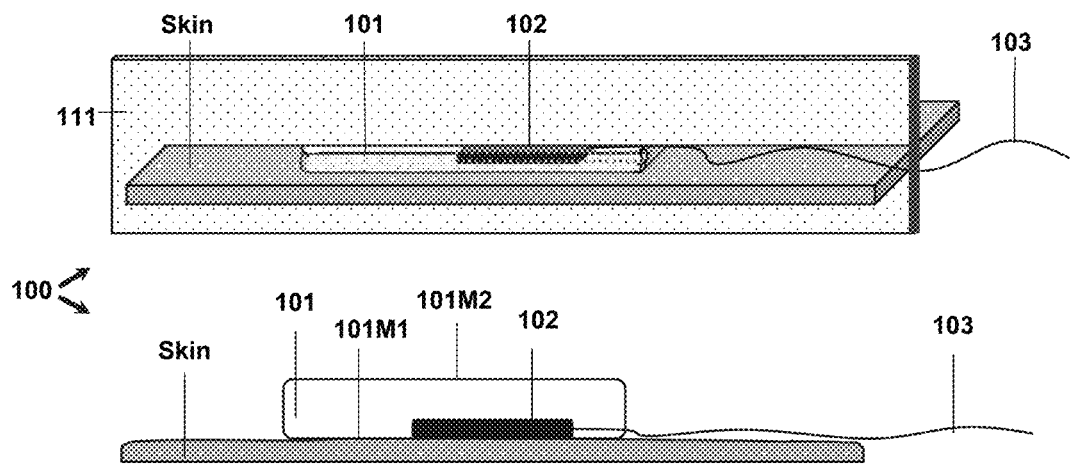
FIG. 1E
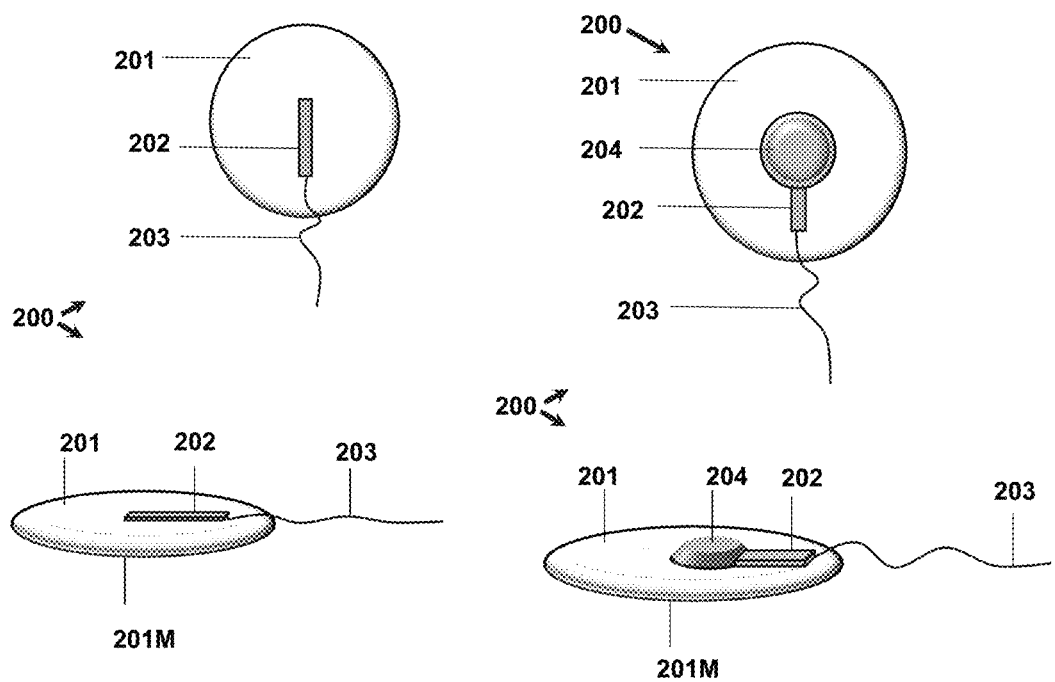
FIG. 2A
FIG. 2B

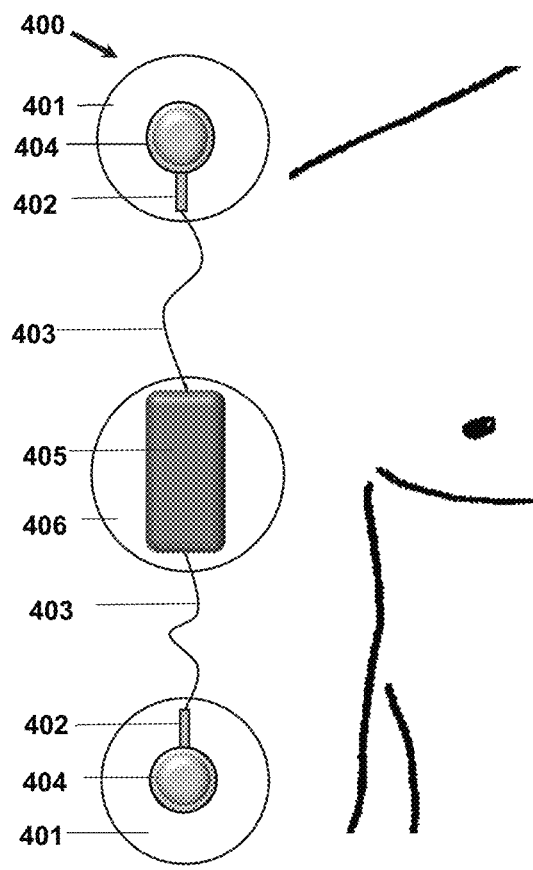
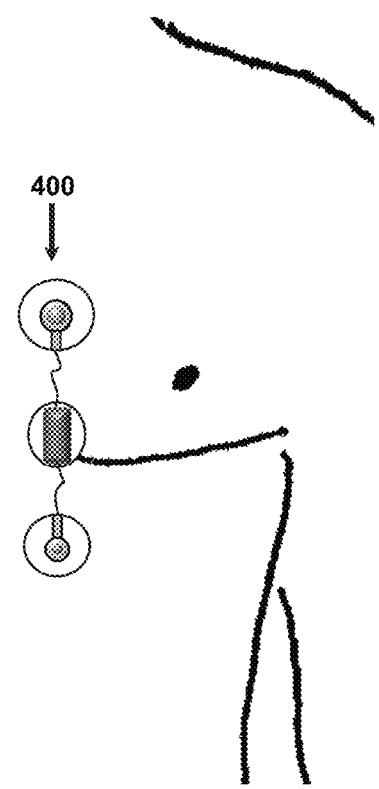
FIG. 4E
FIG. 4F

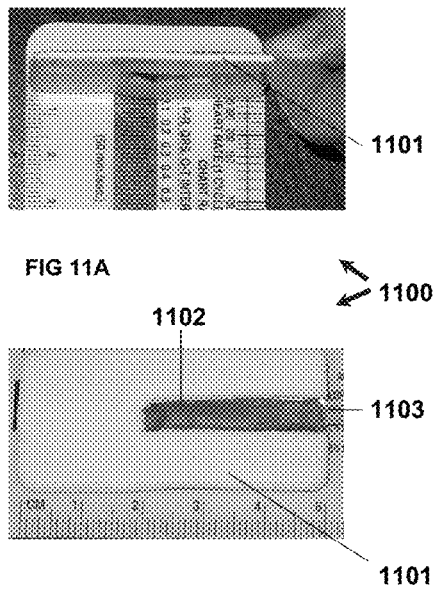
FIG 11A
FIG 11B
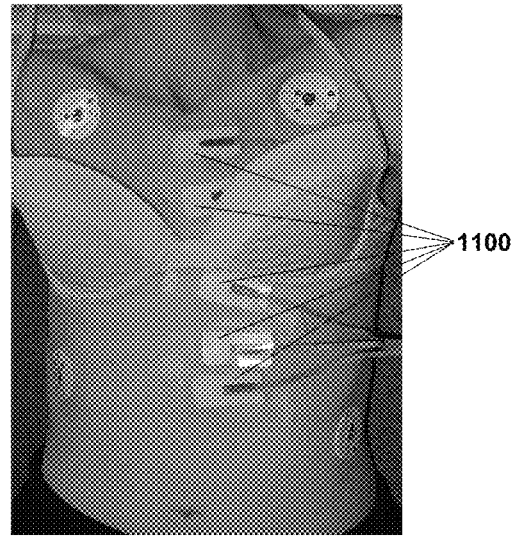
FIG. 11C
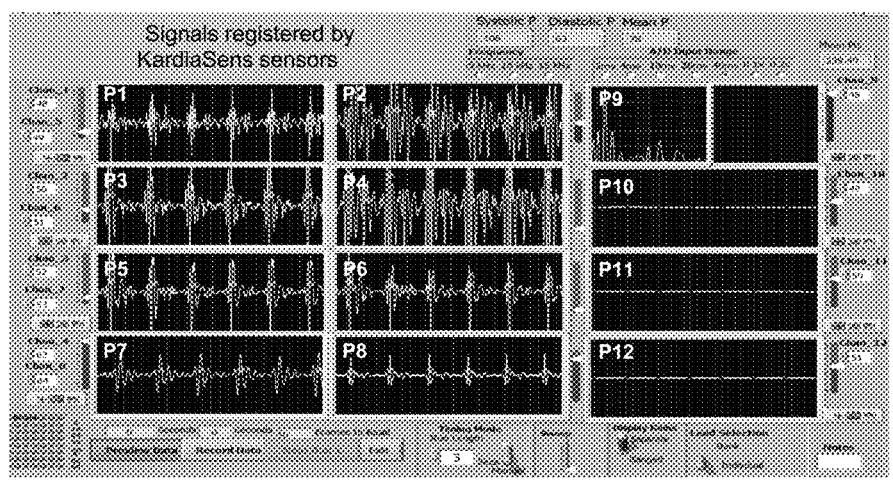
FIG. 11D

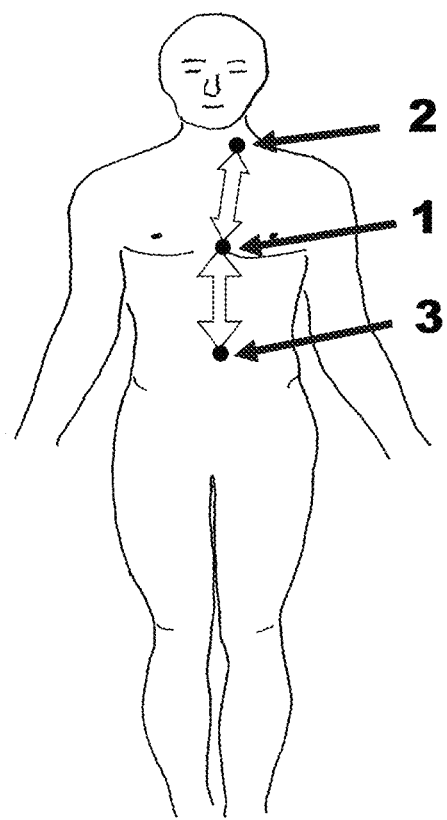
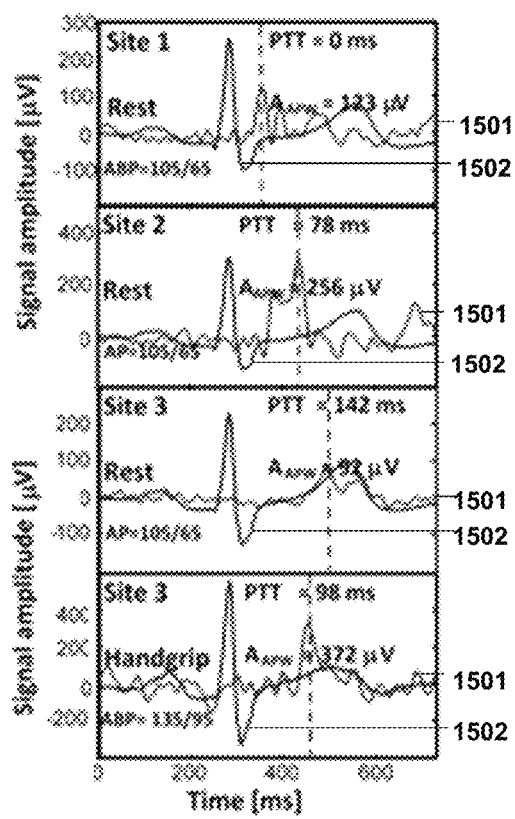
FIG. 15A
FIG. 15B

TRACKING CARDIAC FORCES AND ARTERIAL BLOOD PRESSURE USING ACCELEROMETERS

CROSS-REFERENCE TO RELATED APPLICATIONS

This application is a continuation-in-part of pending U.S. patent application Ser. No. 14/196,738, filed Mar. 4, 2014, which is a continuation-in-part of application Ser. No. 13/017,043, filed Jan. 30, 2011 (now U.S. Pat. No. 8,706,464), which are incorporated herein by reference. This application also claims the benefit of U.S. Provisional Application No. 62/442,371, filed Jan. 4, 2017, which is incorporated herein by reference.

STATEMENT REGARDING FEDERALLY SPONSORED RESEARCH OR DEVELOPMENT

This invention was made with government support under the grant R43HL114277 awarded by the National Institutes of Health. The government has certain rights in the invention.

FIELD OF THE INVENTION

This invention relates to the field of biomedical sensors and sensor manufacturing processes, methods, and systems for testing and monitoring cardiovascular activity, in particular: (i) integrated sensors, circuits, and systems for physiological sensing of cardiovascular activity; (ii) methods and systems for the evaluation and tracking of arterial blood pressure in the central arteries; (iii) wearable monitoring devices for tracking cardiovascular activity, cardiovascular risk stratification, exercise, and wellness training; (iv) evaluation of mechanical forces generated by the heart and its specific parts, as well as the degree of synchronicity between the forces generated by different parts of the cardiac muscle; and (v) diagnosis, monitoring, and management of heart failure (HF), including guidance and optimization of resynchronization pacing therapy.

BACKGROUND OF THE INVENTION

Cardiac Forces, HF, and Pulmonary Hypertension

Each year, over 500,000 people receive a diagnosis of HF in the US alone; approximately 50% of them die within 5 years of diagnosis (Bui, A L; Horwich, T B; Fonarow, G C. Epidemiology and risk profile of heart failure. Nature Reviews Cardiology. 2011; 8:30-41. doi:10.1038/nrcardio.2010.165. PMC 3033496 Freely accessible. PMID 21060326). Timely diagnosis and management of HF are crucial for preventing life-threatening complications such as cardiac arrhythmias (e.g., ventricular fibrillation) and pulmonary edema.

The main sign of HF is impairment of the cardiac mechanical (pumping) activity, which may include decrease in its ejection fraction, diastolic relaxation, and loss of synchrony between the cardiac contractions in different regions of the heart (regional cardiac dyssynchrony). Right-sided HF may be caused by an increase of blood pressure in the pulmonary (lung) vasculature (pulmonary hypertension) or increased vascular resistance in the lungs. The detection, diagnosis, and monitoring of such abnormalities in mild, early-stage cases are challenging.

Several treatment options have recently been developed to improve cardiac pumping activity. In particular, cardiac resynchronization therapy (biventricular pacing), which restores the synchrony of cardiac contractions in the two cardiac ventricles, has become an important treatment modality for HF patients. Treatment success depends on optimally positioned pacing electrodes and precisely timed pacing stimuli which restore the synchrony of cardiac contractions. A number of methods have been applied for these purposes, including echocardiography (cardiac ultrasound), cardiovascular magnetic resonance imaging (MM), and other tests. However, determining the patients who can benefit from cardiac resynchronization therapy, finding the optimal sites for placing the pacing electrodes, and determining the optimal timing for the pacing stimuli remain challenging.

One method for monitoring cardiac mechanical forces is ballistocardiography (BCG). BCG has been used for over 60 years; in 1953, Gubner et al. described changes in the BCG waveforms associated with myocardial disease and HF: reduction or disappearance of the I wave, smaller and delayed J peak, large diastolic waves associated with abnormal return flow to the heart, and a prominent H wave, reflecting sudden deceleration of return flow with the onset of ventricular contraction (Gubner R S, Rodstein M, Ungerleider H E. Ballistocardiography; an appraisal of technic, physiologic principles, and clinical value. Circulation 1953; 7:268-86). However, BCG has been limited to a "lumped," single-waveform representation of cardiac forces using a single sensor positioned at a single site. Furthermore, the prior-art BCG devices were non-portable (e.g., a bed, platform, weighting scale).

The parent Shusterman U.S. Pat. No. 8,706,464 (which claims the benefit of the US Provisional Application Ser. No. 61300004) discloses the first application of miniaturized, wearable, accelerometer-based sensors for tracking cardiovascular activity on the torso (including the thorax and abdomen), as well as on other locations on the body surface, including peripheral vessels (on the extremities, radial artery, hands, fingers, legs, feet, or toes), neck (e.g., carotid artery), and/or head, to measure the dynamical patterns of pressure waves in those peripheral vessels. In particular, a sensor can be placed on the torso instead of (or in combination with) a sensor placed more peripherally (e.g., extremities, fingers, toes, neck, or head). A combination of sensors placed over the central arteries (e.g., the aorta) and non-central (peripheral) arteries (e.g., brachial artery, wrist or digital arteries) provides the basis for comparing the patterns of cardiovascular activity (arterial-pressure [AP] wave) parameters in the central and peripheral vessels and for separating peripheral vascular activity from systemic blood pressure.

As disclosed in the parent Shusterman U.S. Pat. No. 8,706,464, placing the sensor for measuring the pressure pulse wave on the torso eliminates vascular-activity confounders (which are present in the peripheral arteries) and simplifies the detection, separation, and tracking of non-local (systemic) patterns of AP dynamics, which are primarily associated with changes in cardiac output, heart rate, and systemic vascular activity. In addition, placing the sensor in the vicinity of central blood vessels also facilitates the detection of changes in those blood vessels, including an aneurism or atherosclerotic changes in the abdominal aorta, portal vessels, or pulmonary vessels.

Arterial Blood Pressure Measurement

Over 40 million Americans suffer from hypertension. Timely diagnosis and control of high arterial blood pressure are crucial for preventing life-threatening complications and end-organ damage but have been hampered by the lack of nondisruptive monitors for 24-hour (including essential nighttime) AP tracking. Due to the epidemic proportions of AP abnormalities, a nonobtrusive, cuff-free AP monitor will have a significant, lasting impact on the lives of millions of Americans, particularly those with cardiovascular risk factors and chronic cardiovascular diseases.

Cuff-based AP measurements disrupt normal sleep. An alternative, cuff-free AP measurement using the analysis of the AP waves in the peripheral arteries has been hampered by the temporal variability of the smooth muscle tone in the peripheral vasculature, which obscures the relationship between the central (systemic) and peripheral AP wave. Due to such variability, accurately estimating AP from the AP velocity (or its inverse, the pulse-transit time [PTT]) in the peripheral arteries has proved to be difficult. The parent Shusterman U.S. Pat. No. 8,706,464 and pending U.S. patent application Ser. No. 14,196,738 disclose the first application of wearable accelerometer-based sensors (specifically, microelectromechanical systems [MEMS] accelerometers) positioned on the torso for tracking arterial blood pressure in the central arteries.

Electrocardiographic Body-Surface Mapping and Electrocardiographic Imaging

Electrocardiographic body-surface potential mapping refers to electrocardiogram (ECG) measurements at multiple sites on the body surface (torso) to construct detailed distributions (maps) of the ECG waves (electrical potentials) and/or their parameters, such as isochronal maps (the spatial distributions of the times of occurrence of specific ECG parameters, e.g., waves, peaks, or troughs) or ECG-wave propagation velocity maps obtained from such measurements. ECG imaging refers to the combined measurements of the body-surface ECG from multiple sites, as well as the measurements of cardiac anatomy (e.g., using computed tomography [CT] images) to reconstruct the electrophysiological activity (or its parameters) on the surface of the heart (e.g., the epicardium, endocardium, and/or myocardium). Currently, there are no practical techniques for simultaneous mapping of ECG and cardiac mechanical forces on the torso surface.

SUMMARY OF THE INVENTION

This invention is directed to sensors and sensor-manufacturing processes, systems, devices (apparatuses), and methods for the evaluation and monitoring of cardiovascular activity, including the mechanical forces (accelerations) generated by the heart muscle, using accelerometer-containing sensors positioned on the body surface, including the torso, abdomen, limbs, neck, and head. Preferably, the sensors of this invention use modular design, which streamlines the development, modification, and manufacturing process. The modular sensors of this invention include an electronic component (module, element) comprising one or more electronic elements (e.g., accelerometers, BCG sensors, ECG sensors, electromyographic [EMG] sensors, acoustic [acoustoelectric, electroacoustic] sensors, electrical-impedance sensors, galvanic-skin-response [GSR] sensors, temperature sensors, blood-pressure sensors, heart-rate sensors, photoplethysmographic sensors, ultrasound [ultrasonic] sensors, pressure sensors, piezoelectric sensors, electrical resistors, capacitors, filters, power supplies, microcontrollers, microprocessors, field programmable gate arrays [FPGAs], programmable logic devices [PLDs], complex programmable logic devices [CPLDs], memory components, storage components, communication components, or wireless-communication components) and one or more mechanical components (e.g., housing and/or membrane). The modular design also facilitates the development, testing, and production of interchangeable sets of modules (e.g., housing, membrane, sensing elements, filters, memory, wireless-communication components, microcontrollers) for different body sizes (e.g., small, medium, large, and pediatric sizes), body shapes, different anatomical locations (e.g., intercostal spaces, parasternal region, precordial region, subxiphoid region), or genders. The interchangeable components provide flexibility of use to enable connecting, disconnecting, interchanging, and/or replacing one or more modules (components or elements), which may be designed for single use or multiple uses (reusable component).

This invention includes sensors, systems, methods, and wearable devices that are useful in several areas of medicine, healthcare, home monitoring, wellness, exercise, and fitness training, including: (i) integrated sensors, circuits, and systems for the physiological sensing of cardiovascular activity; (ii) methods and systems for the evaluation and tracking of arterial blood pressure in the central arteries; (iii) wearable monitoring devices for tracking cardiovascular activity, cardiovascular risk stratification, exercise, and wellness training; (iv) evaluation of the mechanical forces generated by the heart and its specific parts, as well as the degree of synchronicity between the forces generated by different parts of the cardiac muscle; and (v) diagnosis, monitoring, and management of left-sided and/or right-sided HF, including guidance and optimization of resynchronization pacing therapy.

By sampling the forces (accelerations) at different locations on the torso surface (and/or other locations on the body surface, including the limbs, neck, and head) and evaluating the associated BCG features (peaks and/or waveforms) at each location, as well as the spatiotemporal relationships (e.g., time intervals) between the BCG features at different locations and/or between the ECG and BCG features, this invention enables more accurate evaluation of physiological activity than the prior art. In particular, this invention provides a practical solution for the combined electromechanical mapping of cardiovascular activity (i.e., body-surface mapping of cardiac electromechanical activity or cardiac electromechanical imaging), including ECG and mechanical forces of the heart. Specifically, this invention discloses systems, methods, and devices for registering (measuring, sensing, assessing, estimating, evaluating, monitoring, tracking, or otherwise quantifying) one or more of the following types of physiological activity (forces, patterns, features, waveforms, maps), using accelerometer-containing sensors at different locations on the torso surface:

a. Contractile activity (forces) and movements of the heart (cardiac or cardiovascular activity), including one or more features from the following list:
   A. Ejection fraction;
   B. Cardiac output;
   C. AP wave in one or more central arteries as disclosed in the parent-case documents, which include: (i) pending U.S. patent application Ser. No. 14/196,738, filed Mar. 4, 2014, which is a continuation-in-part of (ii) application Ser. No. 13/017,043, filed Jan. 30, 2011 (now U.S. Pat. No. 8,706,464), and (iii) U.S. Provisional Application No. 62/442,371, filed Jan. 4, 2017, which are incorporated herein by reference.

b. Mechanical forces, their spatial synchrony, regional asynchrony and/or delay in specific regions of the heart, including the left and right ventricle; apex; base; the anterior, posterior, lateral, and inferior walls of the left ventricle; interventricular septum; the anterior, inferior, and lateral (free) wall of the right ventricle; and the left ventricular and the right ventricular segments (basal, mid, and apical);
c. Respiratory activity, its symmetry/asymmetry, amplitude, frequency, pauses, snoring, sleep-disordered breathing, apnea, and hypopnea;
d. Movements of the body parts, including limbs, neck, and head;
e. Chest muscle contractions;
f. Changes in body position (supine, lying on the left side, lying on the right side, sitting, standing);
g. Changes in activity level (staying still, walking, running, and quantifying the walking speed or the running speed);
h. Mechanical activity of gastrointestinal (GI) organs; and
i. Speech and speech patterns.

The sensors of this invention may be placed on the torso (including the thorax and abdomen), as well as other locations on the body surface, including peripheral vessels (e.g., on the extremities, radial artery, hands, fingers, legs, feet, or toes), neck (e.g., carotid artery), and/or head, to measure the dynamical patters of the cardiac forces, cardiovascular mechanical activity, and/or pressure waves in those peripheral vessels. In particular, the sensor can be placed on the torso instead of (or in combination with) a sensor placed more peripherally (e.g., extremities, fingers, toes, neck, or head). A combination of sensors placed over the central arteries (e.g., the aorta) and non-central (peripheral) arteries (e.g., brachial artery, wrist or digital arteries) provides the basis for comparing the patterns of cardiovascular mechanical activity, cardiac forces, and/or AP-wave parameters in the central and peripheral vessels and for separating peripheral vascular activity from systemic blood pressure.

Placing the sensor for measuring blood pressure or blood-pressure wave (which is also referred to as the pulse wave or pulse pressure) on the torso eliminates vascular-activity confounders (which are present in the peripheral arteries) and simplifies the detection, separation, and tracking of non-local (systemic) patterns of cardiac forces and/or blood-pressure dynamics, which are primarily associated with changes in cardiac output, heart rate, and systemic vascular activity. In addition, placing the sensor in the vicinity of the central blood vessels also facilitates the detection of changes in those blood vessels. For example, placing the sensor in the vicinity of the abdominal aorta will facilitate the detection of an aortic aneurism and/or atherosclerotic changes (e.g., plaque, stiffening) in the abdominal aorta. Similarly, placing the sensor for tracking the pressure wave in the vicinity of the portal vessels will improve the detection and tracking of portal pressure changes and early detection of the dynamic patterns associated with portal hypertension, cirrhosis, or other liver disorders. Similarly, placing the sensor for tracking the pressure wave in the vicinity of the pulmonary vessels (large pulmonary arteries/veins) will improve the tracking of pressure changes in the pulmonary-artery/venous system (e.g., pulmonary hypertension). In particular, the sensor of this invention can be placed over the right lung (to provide some distance from the heart).

In some embodiments, the accelerometer-containing sensors include one or more sensors selected from: single-axial accelerometer, three-axial accelerometer, MEMS accelerometer (e.g., ADXL330, Analog Devices, Norwood, Mass. or LIS344ALH, STMicroelectronics, Geneva, Switzerland), and six-axial motion sensors (e.g., ICM-20609, TFK-InvenSens, San Jose, Calif.). Some embodiments include high-fidelity sensors, such as high-resolution MEMS accelerometer sensors, for high-fidelity tracking and/or mapping of cardiac mechanical or electromechanical activity.

Some embodiments of this invention include a combination of sensors (or modular, multicomponent, combined, integrated, integral sensors and/or transducers), which include housing (enclosure, cover) and one or more physiological sensing elements selected from:
a. Accelerometer-containing sensors for measuring mechanical activity, including BCG, respiratory movements, changes in body position, and movement of one or more body parts (torso, limb, neck, head), described above;
b. EMG electrodes (sensors);
c. ECG electrodes (sensors);
d. Transthoracic electrical impedance (plethysmography) sensors;
e. Photoplethysmographic sensors;
f. Temperature sensors;
g. GSR sensors;
h. Ultrasound (ultrasonic) sensors;
i. Acoustic (acoustoelectric, electroacoustic) sensors;
j. Pressure sensors; e.g., pressure-sensitive film sensors (e.g., Tekscan, Boston, MA);
k. Blood-pressure sensors;
l. Heart-rate sensors; and
m. Piezoelectric sensors.

The sensors of this invention are manufactured, attached to the skin of the torso, and/or placed in clothing using one or more of the following materials and fabrication techniques:
a. Conformal (flexible or stretchable) housing (enclosure for the sensor's electronic circuitry) using conformal (flexible or stretchable) materials, such as polyimide, transparent conductive polyester, a thin silicon substrate, and/or other plastics or polymers. The housing may include one or more flexible membranes (diaphragms), which are adapted to provide firm contact with:
A. The skin surface of an individual subject on one (outer) side; and
B. The accelerometer-containing circuitry on the other (inner) side, thus transmitting movements of the body surface to the accelerometer-containing circuitry.
b. One or more of the disclosed sensors can be mounted (attached, coupled) directly to the skin of the torso using an adhesive material (e.g., the adhesive material or conductive-adhesive gel used for attaching disposable ECG electrodes to the skin).
c. Conformal (flexible or stretchable) sensors using conformal (flexible or stretchable) electronics (flex circuits, flexible printed wiring, flex print, or flexi circuits) embedded in, printed on, or attached to conformal (flexible or stretchable) plastic or polymeric substrate, such as polyimide, transparent conductive polyester, or a thin silicon substrate.
d. Conformal (flexible or stretchable) electronics providing close (mechanically transparent) contact with the surface of the torso. Flexible electronic circuits are now manufactured by a number of companies, including Flexible Circuit Technologies (Minneapolis, Minn.). The flexible substrate can be configured to conform (couple) to the surface of the torso of a human or animal. In some embodiments, one or more sensor components (the terms module, component, element, circuit, and unit are used interchangeably throughout this document) is embedded in one or more flexible substrates. In various examples, ECG (or EMG) electrodes are integrated (integral) with an accelerometer-containing sensor or are made separate/separable from the said accelerometer-containing sensor.
   e. Semi-rigid sensors (rigid-flex circuits) providing a combination of flexibility and rigidity. Such sensors are also available from a number of companies, including Flexible Circuit Technologies. The semi-rigid sensors are used in some embodiments to provide amplification of the cardiovascular signals and reduction of ambient noise and artifacts by spatial averaging of the semi-rigid materials. In some embodiments, the semi-rigid materials are combined with the amplifying membrane, adhesive materials, and electronic housing.
   f. Rigid sensors built using rigid materials (e.g., fiberglass, epoxy resin, copper, paper-reinforced phenolic resin).
   g. A combination of two or more materials selected from rigid, semi-rigid, and flexible sensors.

The sensors are assembled or incorporated into one or more of the following forms or arrangements:
   a. Two or more individual sensors, e.g., one or more accelerometer-containing sensors, one or more ECG sensors/electrodes, one or more EMG sensors/electrodes, one or more respiration sensors/electrodes, one or more transthoracic impedance sensors/electrodes;
   b. One or more sensor arrays (sets);
   c. One or more skin patches, which in some embodiments are shaped like an hourglass (e.g., with the longer side placed along the sternum) or other geometric form with rounded edges or corners, including a rectangle, a square, a rhombus, star, or circle;
   d. Clothing (e.g., shirt, sports bra, tank top);
   e. Body band;
   f. Torso strap;
   g. Torso belt;
   h. Headband (e.g., with the sensors placed over the temporal artery and/or its branches on the forehead);
   i. Wristband (e.g., with the sensors positioned over the radial artery);
   j. Glove (e.g., with the sensors positioned over the digital arteries);
   k. Neck band (e.g., with the sensors positioned over the carotid arteries);
   l. Leg bandage or strap (e.g., with the sensors placed over the femoral or tibial arteries);
   m. Ankle and/or foot bandage or sock (e.g., with the sensors positioned over the dorsalis pedis or foot-arch arteries).

In some embodiments, the sensor arrangement includes one or more components selected from the following list:
   a. Two or more sensors of the same type (e.g., accelerometer-containing sensors) for registering mechanical movements/accelerations at different locations simultaneously or substantially simultaneously;
   b. Two or more sensors of different types (e.g., an accelerometer-containing sensor for registering mechanical movements/accelerations and one or more ECG sensors/electrodes) for registering both accelerations and ECG simultaneously or substantially simultaneously.

In some embodiments, the sensor arrangements also include one or more components (which are attached to the sensor or embedded into the sensor's substrate) selected from the following list:
   a. One or more data-acquisition components, which include one or more analog-to-digital (A/D) converters;
   b. One or more microprocessors, which are communicatively coupled to one or more sensor components and configured to execute and/or control one or more instructions (code, firmware, or software) selected from:
      A. Measurement of physiological activity;
      B. Signal processing (filtering, conditioning, transforming, or averaging);
      C. Data storage;
      D. Data communication;
      E. Data analysis;
      F. Therapy or action triggering.
   c. Preferably, one or more storage (memory) components for storing the measurement data obtained from one or more sensors, e.g., micro multimedia card (MMC) or micro secure digital (SD) card;
   d. Preferably, one or more signal-processing/conditioning circuitries for reducing noise and/or improving signal quality; e.g., analog filtering using one or more capacitors and/or resistors;
   e. Preferably, one or more wireless-communication components. The wireless-communication component is operable to transmit data indicative of the measurements obtained by one or more sensors.
   f. Preferably, one or more data-transmission components, ports, or connectors (e.g., serial port, USB port, or cable connector) for data transmission and/or programming the one or more microprocessor components;
   g. One or more power supplies;
   h. Preferably, one or more therapy (action) components configured to provide medical (e.g., medicinal or non-pharmacological/pacing) treatment based, at least in part, on the measurements obtained by the sensor. The therapeutic component can initiate (trigger) a visual, audio, or tactile stimulus to provide an indication of an important physiological event or change and/or to remind the individual to take a medication or contact a healthcare professional.

Systems and Devices

In some embodiments, systems and devices of this invention include one or more components selected from the following list:
   a. One or more sensors (e.g., sensors containing accelerometers, ECG sensors, EMG sensors, temperature sensors, piezoelectric sensors, GSR sensors, heart-rate sensors, pressure sensors, blood-pressure sensors, ultrasound sensors, acoustic sensors);
   b. One or more data-acquisition components, which include one or more A/D converters;
   c. One or more control components, such as microprocessor, microcontroller, FPGA, CPLD, or PLD, which are electrically (communicatively) coupled to the one or more sensor components and configured to execute and/or control one or more instructions (code, firmware, or software) selected from:
      A. Measurement of physiological activity;
      B. Signal processing (filtering, conditioning, transforming, or averaging);
      C. Data storage;
      D. Data communication;
      E. Data analysis;
      F. Therapy initiation or action (response) triggering;
   d. Preferably, one or more storage (memory) components for storing executable instructions for the control component (e.g., data-acquisition parameters), and/or the measurement data obtained from one or more sensors, e.g., MMC or micro SD card;

e. Preferably, one or more signal-processing/conditioning circuits for reducing noise and/or improving signal quality, e.g., analog filtering using one or more capacitors and/or resistors;
f. Preferably, one or more wireless-communication components. The wireless-communication component is electrically coupled with the control component and configured to perform one or more operations selected from:
   A. Transmitting data indicative of the measurements obtained by one or more sensors; and
   B. Receiving executable instructions for the control component.
g. Preferably, one or more data-transmission components, ports, or connectors (e.g., serial port, USB port, or cable connector) for data transmission and/or programming the one or more microprocessor components;
h. Preferably, one or more power supplies operable to power one or more components selected from: a storage component, control component, sensor component, (wireless) communication component, and A/D component;
i. Optionally, one or more therapy (action) components configured to provide a response/action (e.g., pharmacological or non-pharmacological treatment) based, at least in part, on the measurements obtained by the sensor; such a response may include one or more actions from the following list:
   A. Initiating (triggering) a visual, audio, text, or tactile stimulus, feedback, or message to provide an indication of an important physiological event, change, update, reminder, and/or advice to take a medication or to contact a healthcare professional;
   B. Initiating (triggering) a non-pharmacological treatment, e.g., cardiac pacing, cardiac defibrillation, cardioversion, or cardiac resynchronization pacing;
   C. Sending information (indicative of an individual's health status) to a healthcare professional via the wireless-communication component;
   D. Initiating (or discontinuing, or adjusting the dose or frequency of) injection of a drug or other biological, chemical, or other material, or any combination thereof
j. Optionally, one or more receiving modules (or stations) which in some embodiments are implemented using one or more computing devices selected from: a smart phone, a computer tablet, a personal computer, a computer server, or an Internet server (cloud), and which includes one or more components from the following list:
   A. One or more communication components, ports, or connectors (e.g., a USB port, serial port, or connector) for communicating with the sensor component using one or more wireless or cable connections;
   B. One or more control components, such as a microprocessor, microcontroller, FPGA, or CPLD, which is communicatively coupled to the one or more sensor components and configured to execute and/or control one or more instructions (code, firmware, or software) selected from:
      1. Measurement of physiological activity;
      2. Signal processing (filtering, conditioning, transforming, or averaging);
      3. Data storage;
      4. Data communication;
      5. Data analysis;
      6. Therapy or action triggering;
   C. Optionally, one or more displays for displaying one or more parameters of the data registered by the sensor or one or more parameters derived from those data;
   D. Optionally, one or more printers for printing one or more parameters of the data registered by the sensor or one or more parameters derived from those data.

In some embodiments, the systems of this invention are fabricated using one or more components selected from: an application-specific integrated circuit (ASIC), FPGA, CPLD, and PLD.

The systems, methods, and devices (apparatuses) of this invention are useful for the diagnostic evaluation of cardiac mechanical activity in patients with cardiovascular diseases, including left-sided and/or right-sided HF, pulmonary hypertension, coronary artery disease, and valve defects; they also provide an accurate tool for the evaluation of respiratory activity, including breathing frequency, depth, symmetry, sleep-disordered breathing, apnea, hypopnea, and other types of physiological activity. The invention provides the know-how for gathering (more accurately than prior art) one or more types of information selected from:
   a. Accurate localization of the cardiac regions of abnormal (reduced, delayed, dyssynchronous) activity;
   b. Tracking (monitoring) changes in cardiac function over time, including one or more features from the following list:
      A. Ejection fraction;
      B. Cardiac output;
      C. AP wave in one or more central arteries as disclosed in the parent-case documents;
   c. Optimization of cardiac biventricular resynchronization pacing by determining pacing times and locations for the pacing electrodes that improve the BCG features and cardiac force distributions described above;
   d. Monitoring an individual's compliance with respect to a particular medication, tracking the effects of pharmacological and non-pharmacological treatment, and optimizing treatment strategy and/or medication dosage;
   e. Maps (distributions) of the mechanical forces (movements, accelerations) generated by the heart on the surface of the torso; the maps may be obtained using:
      A. Preferably, two or more sensors (containing accelerometers) to sample body-surface accelerations at the sensor locations simultaneously, or
      B. One sensor (containing an accelerometer) to sample body-surface accelerations by placing the sensor at different sites, one at a time, and sampling the data from each site consecutively (non-simultaneous sampling).
   f. Maps (distributions) of the differences in the features and patterns of accelerations associated with cardiovascular activity on the torso surface, including the features and patterns described in sections a, b, and c above;
   g. Maps (distributions) of the mechanical forces (accelerations) generated by the heart (including those described in sections e and f above) that include neck, head, and/or limbs;
   h. Accurate evaluation of cardiovascular status in healthy individuals, as well as in those with cardiovascular risk factors;
   i. Maps (distributions) of the respiratory movements on the surface of the torso, which improve evaluation of respiratory movements, sleep-disordered breathing, detection of sleep apnea and hypopnea, and differentiation of central sleep apnea from obstructive sleep apnea;
j. Accurate tracking of changes in body position during sleep;
k. Accurate tracking of physical activity, including walking and running speed (number of steps);
l. Accurate tracking of movements related to speech and speech recognition.

Some embodiments of this invention include analysis of the BCG waveforms, the $1^{st}$ derivative of the BCG waveforms with respect to time (also referred to as the rate of change of acceleration, jerk, jolt, surge, or lurch), the $2^{nd}$ derivative of the BCG waveforms with respect to time (i.e., the $1^{st}$ derivative of the BCG jerk with respect to time), and the integral of the BCG waveforms with respect to time. In addition, some embodiments of this invention include analysis of the ECG waveforms, EMG waveforms, respiratory (breathing) movements, movements of body parts (limbs, neck, head), physical activity, GI activity, and speech patterns. Some non-limiting examples of the specific features and parameters determined by the systems, methods, and devices of this invention include:

a. One or more parameters determined from one or more sensor locations (signals), including: the time of occurrence, duration, and amplitude of one or more BCG peaks/waves (e.g., H, I, J, K, L peak/wave), the time interval between two or more BCG peaks, the time interval (delay) between one or more ECG peaks (P, Q, R, S, T, U ECG wave/peak) and one or more BCG waves/peaks, the time interval between one peak (in two or more signals) or two or more peaks (in one or more signals) of the jerk of BCG waveforms, the time interval between one or more peaks of the jerk of BCG waveforms and one or more peaks of BCG waveforms, the time interval between one or more peaks of the jerk of BCG waveforms and one or more ECG peaks, the time interval between two or more peaks of the $1^{st}$ derivative of the BCG jerk, the time interval between one or more peaks of the $1^{st}$ derivative of the BCG jerk and one or more peaks of BCG waveforms (signals) or one or more ECG peaks at different sensor locations.

b. One or more parameters determined using a mathematical relationship that includes values obtained from two or more sensor locations (signals), including the time interval between the occurrence of one or more BCG peaks (e.g., BCG peak I) in two or more sensor locations (signals), and one or more time intervals between the occurrence of two or more BCG peaks determined in two or more sensor locations (signals); the delay between the time of occurrence of the same BCG wave/peak at different sensor locations; and the delay between the time of occurrence of the same wave/peak of the BCG jerk at different sensor locations. Examples of a mathematical relationship that includes values obtained from two or more sensor locations (signals) include:

A. Difference or ratio calculated between the time of occurrence (delay, interval) of a BCG peak registered by two or more sensors;
B. Difference or ratio calculated between the amplitude of a BCG peak registered by two or more sensors;
C. Difference or ratio calculated between the time of occurrence (delay, interval) of a peak of the BCG jerk registered by two or more sensors;
D. Difference or ratio calculated between the amplitude of a peak of the BCG jerk registered by two or more sensors;
E. Average (arithmetic or geometric), sum, or median value of one or more parameters of data obtained from two or more sensors to reduce noise and/or increase signal quality (signal-to-noise ratio) with respect to one or more physiological signals of interest described in the preceding paragraphs.

Manufacturing Process

This invention also discloses a novel sensor-manufacturing process, herein referred to as delayed-embedding, modular (DEM) manufacturing, in which the manufacturing of an ultra-thin, conformal (flexible, stretchable) sensor is structured in three stages:

a. Manufacturing of the sensor housing using the materials described below (see DESCRIPTION OF THE PREFERRED EMBODIMENTS) and containing a slot (pocket, sheath) for fitting the electronic component containing one or more accelerometers;
b. Manufacturing of the electronic component containing one or more accelerometers, which may include:
A. Manufacturing of the miniature printed circuit board (PCB), which may be flexible, semi-rigid, or rigid; and
B. Assembling electronic components (e.g., accelerometer, resistors, capacitors, filters, memory [storage], microcontroller, power supply) on the PCB;
c. Connecting (embedding, inserting) the electronic component into said slot in said housing and securing said electronic component using one or more locking mechanisms described below (see DESCRIPTION OF THE PREFERRED EMBODIMENTS).

The advantages of DEM manufacturing include:
a. Fast, inexpensive, flexible, and efficient production of the sensors (in small or large quantities) without the need to modify or reorganize the manufacturing process and facilities in order to combine chemical manufacturing (for producing the housing) and electronic manufacturing (for producing the electronic component containing one or more accelerometers);
b. Flexibility to modify the housing or the electronic component separately, thus reducing the time and cost for product modifications; this includes:
A. Modifying the size and/or thickness of the flexible membrane;
B. Modifying the size and/or thickness of the entire housing;
C. Modifying the size and/or design of the electronic component (e.g., filters, connectors);
c. Fast and efficient testing (and replacement if necessary) of the electronic component;
d. Manufacturing multiple types of housing, which include additional sensor elements (e.g., ECG, EMG);
e. Production of multiple single-use or reusable membranes optimized for different anatomical sites, which can be quickly connected or disconnected/replaced at any time by manufacturing or service personnel or by users;
f. Production of multiple single-use or reusable electronic components (containing various accelerometers, filters, and/or other electronic elements) optimized for different anatomical sites, which can be quickly connected or disconnected/replaced at any time by manufacturing or service personnel or by users;
g. Fast and efficient embedding (integrating, incorporating) of the sensors, systems, and devices of this invention into (or attaching to) clothing, such as wearable vests, patches, bands, body straps, and/or belts as described below (see DESCRIPTION OF THE PREFERRED EMBODIMENTS).

Note that the sensors, systems, and devices of this invention may be manufactured by other available manufacturing processes in addition to the DEM manufacturing process described above.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present invention when taken in connection with the accompanying drawings and the appended claims.

BRIEF DESCRIPTION OF THE DRAWINGS

A full understanding of the invention can be gained from the following description of the preferred embodiments when read in conjunction with the accompanying drawings in which:

FIGS. 1A-E are drawings of an example sensor of this invention.

FIGS. 2A-B are drawings of two examples of sensors of this invention; one of the examples includes an ECG clip for connecting ECG leads (cables).

FIGS. 4A-H are drawings of examples of: (i) various configurations of the sensors of this invention, and (ii) examples of sensor placements on the surface of a torso.

FIGS. 11A-D are a selection of photographs and data samples obtained from a human subject using a laboratory version of the system of this invention. The photographs include an example sensor of this invention, a human torso with the sensors attached, and a computer display showing the data acquired (streamed) in real time from the sensors of this invention. The photographs were obtained in a laboratory setting.

FIG. 12A: a human torso with the sensors of this invention attached; FIG. 12B: the portable ambulatory-monitoring system (which includes the data-acquisition module, memory, control module, processing module, wireless-communication module, and connecting cables); FIG. 12C: a smart-phone display showing data acquired via wireless link (Bluetooth) and streamed in real time from the system of this invention; and FIG. 12D: the enlarged raw and processed data (signals).

FIGS. 15A-B are examples of the torso-surface placement of the three accelerometer-containing sensors of this invention on the surface of the torso and data sample that was simultaneously registered from these locations using accelerometers and ECG sensors. The signals were used to calculate the PTT, i.e., the time required for the pressure wave to travel between two specific locations in the arterial system. PTT was computed as the time interval or delay between the time of a specific peak (e.g., I peak, or J peak, or the $1^{st}$ time derivatives [jerks] of these peaks, or a combination thereof) registered by the accelerometer-containing sensors at the torso-surface locations shown in the figure. In addition, the pulse-arrival time (PAT) between the R peak of the ECG signal and the largest peak of the acceleration signal, which includes the pre-ejection period and PTT, was also computed. The magnitude of the largest peak ($A_{APW}$) of the acceleration signal was also computed. The signals were recorded at rest and during handgrip.

FIG. 20A shows the theoretically predicted (spatially "regular") distribution of the cardiac-force-generated accelerations of the torso surface and pressure-wave arrival times (isochrones, isochronal map) at different locations in a hypothetical subject without cardiovascular diseases. FIG. 20B shows a theoretically predicted (spatially "irregular") distribution of the cardiac-force-generated accelerations of the torso surface and AP-wave arrival times in a hypothetical subject with cardiovascular disease (e.g., congestive heart failure or pulmonary hypertension).

DESCRIPTION OF THE PREFERRED EMBODIMENTS

This disclosure contains some representative embodiments, which are provided primarily for illustrative purposes and which are not intended to limit the broad aspects of the invention. To that extent, elements and limitations that are disclosed, for example, in the Abstract, Summary, and Description of the Preferred Embodiments, but not explicitly set forth in the claims, should not be incorporated into the claims, singly or collectively, by implication, inference, or otherwise.

Any and all combinations of the features, functions, and concepts discussed in detail herein are contemplated as being part of the inventive subject matter (provided such concepts are not mutually inconsistent). For example, although differing in appearance, the individual systems and devices and functional componentry depicted and disclosed herein can each take on any of the various forms, optional configurations, and functional alternatives described above and below with respect to the other disclosed embodiments, unless explicitly disclaimed or otherwise logically prohibited. Following below are more detailed descriptions of various concepts related to, and embodiments of, inventive methods, devices, and systems for analysis of data indicative of physiological activity, as non-limiting examples, for such applications as diagnosis, treatment, training, and/or clinical purposes. It should be appreciated that various concepts introduced above and discussed in greater detail below may be implemented in any of numerous ways, as the disclosed concepts are not limited to any particular manner of implementation.

Figure 1A:
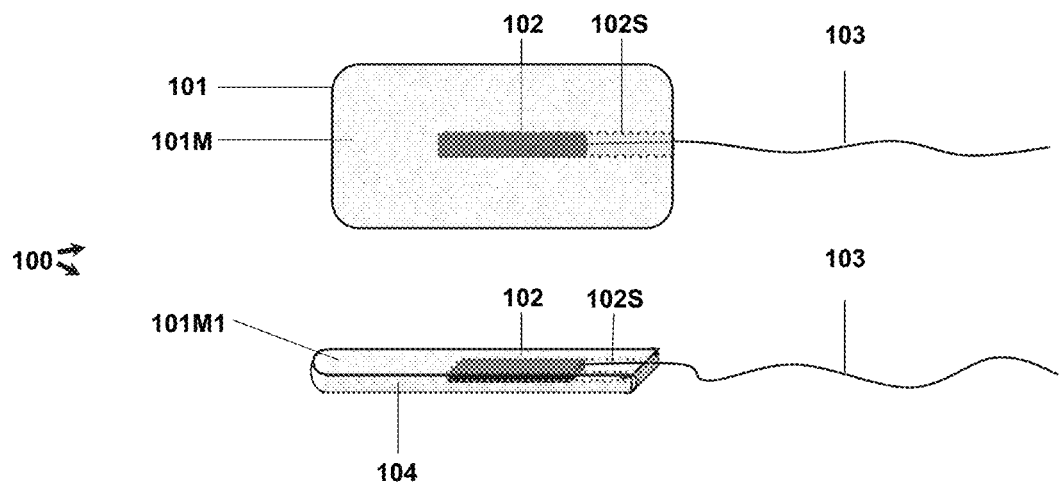

FIG. 1A shows an example of a modular cardiovascular sensor 100 of this invention (also referred to as a KardiaSens™ sensor), which includes a housing 101 with one or more conformal (flexible or stretchable) contact membranes (diaphragms) 101M1 on one or more sides of the housing, the accelerometer-containing electronic circuitry 102, which may have its own housing (e.g., made from heat-shrink tubing, resin, plastic, or polymer) for protecting and securing the circuitry (e.g., a rigid, flexible, or semi-rigid PCB, one or more electrical connectors, one or more electrical wires/cables), electronic components (e.g., one or more accelerometers, resistors, capacitors, filters, power supplies, microcontrollers, PLDs, CPLDs, or FPGAs), and electronic-coupling element 103 (e.g., connecting cable, wire, or connector), which are located inside the housing slot (pocket) 102S. The slot 102S is designed to fit the circuitry 102 (including its shape and dimensions), enabling easy insertion of the circuitry 102 during manufacturing, assembling, or sensor setup (prior to its use). This also allows fast and efficient extraction of the circuitry 102 and subsequent replacement of the housing 101 (which may be designed for single use). The size of the housing 101 may be, for example, 50 mm×25 mm×2 mm; the size of the slot 102S may be, for example, 30 mm×4.5 mm, and the size of the circuitry 102 may be, for example, 20 mm×5 mm×2 mm. A housing of this size and shape provides a good fit for positioning the sensors (with the longer size positioned along the ribs) in the intercostal spaces (i.e., the anatomic spaces between two adjacent ribs), subxiphoid, and upper abdominal area, as well as subclavian and other torso areas.

The housing 101 and/or membrane 101M1 can be made from a thin, conformal (flexible or stretchable) material (film), such as ~50-micron thin polymer material (e.g., polyimide, cellulose acetate, polyesters, silicone, silicone rubber, polyvinyl chloride, polyethylene, polyethylene naphthalate, polyethylene terephthalate, polyethylene copolymers and/or modified polyethylenes, polyetherimide, polycarbonate, polyketones, polypropylene, fluoropolymers, and copolymers, polyurethanes, and/or other plastics, elastomers, thermoplastic elastomers, elastoplastics, thermostats, thermoplastics, acrylates, acetal polymers, biodegradable polymers, cellulosic polymers, nylons, polyacrylonitrile polymers, polyamide-imide polymers, polyarylates, polybenzimidazole, polybutylene, polymethylmethacrylate, polymethylpentene, polyphenylene oxides and polyphenylene sulfides, polyphthalamide, styrenic resins, sulphone based resins, vinyl-based resins, or any combinations of these materials, including a UV curable polymer or a silicone) or semi-rigid material (e.g., a combination of rigid and flexible substrates laminated together, such as epoxy-fiberglass compound, resins, or other types of plastic materials).

The membrane 101M1 can be also made from gas-permeable, lightweight, stretchable on-skin electronics with nanomeshes (Miyamoto A, Lee S, Cooray NF, Lee S, Mori M, Matsuhisa N, Jin H, Yoda L, Yokota T, Itoh A, Sekino M, Kawasaki H, Ebihara T, Amagai M, Someya T. Inflammation-free, gas-permeable, lightweight, stretchable on-skin electronics with nanomeshes. Nature Nanotechnology 2017, doi:10.1038/nnano.2017.125).

A thin metal (e.g., copper or gold) foil or traces, or carbon polymer can be embedded into or attached to the diaphragm to make the membrane (or its parts) electrically conductive if necessary. The membrane 101M1 can be attached to the skin of an individual using an adhesive (e.g., an adhesive or adhesive-gel material used in ECG and EMG electrodes) and/or medical tape.

The membrane 101M1 is attached to the skin of an individual in order to transmit mechanical movements (vibrations, accelerations) of the torso surface to the accelerometer-containing electronic circuitry 102. Note that the membrane's 101M1 size and resistance (which can be adjusted by selecting the membrane's thickness and material's mechanical impedance/resistance) can provide spatial signal averaging and signal amplification (due to the membrane's resonating properties) to improve the signal quality and reduce random noise (improve the signal-to-noise ratio). For example, a 2×1-inch membrane with a thickness of ~50 microns provides an excellent signal-to-noise ratio, as well as convenient placement on the torso area.

The signals generated and amplified by the membrane 101M1 are affected by both the membrane's material properties and the membrane's coupling to the individual's skin. Different types of coupling can be applied to achieve selective amplification and/or damping of specific signals and/or signal frequencies. Some examples of different couplings include:

a. Tight coupling of the membrane's 101M1 entire area to the skin surface;

b. Tight coupling of the membrane's partial area to the skin surface, e.g.,

A. Coupling of the outer area/edge of the membrane 101M1, with freely moving central part (area) of the membrane; or B. Coupling of one side of an outer edge of the membrane 101M1, with freely moving central part (area) and the uncoupled (opposite side) of the membrane.

The central part (area) of the membrane 101M1 can have a concave shape, to provide space for an air pocket between the membrane and the individual's skin. The thickness and/or material properties of the central part (area) of the membrane 101M1 can be different from the membrane's edges. For example, the central area can be thinner than the edges to improve and/or modify its resonating/amplifying/damping properties. The outer area of the membrane 101M1 can be thicker than the central area of the membrane. The outer area can also have an extra rim, to provide space for an air pocket between the membrane 101M1 and the individual's skin. The rim can also facilitate tight skin contact (coupling), because pressure on the central part of the membrane would cause suction of the air pocket between the membrane and the individual's skin. The rim can be made from a flexible material (e.g., polyimide, cellulose acetate, polyester, silicone rubber, polyvinyl chloride, polyethylene naphthalate, polyetherimide, fluropolymers, and copolymers) or semi-rigid material (e.g., a combination of rigid and flexible substrates laminated together, such as epoxy-fiberglass compound, resins, or other types of plastic materials).

The housing 101 can be a single-use, disposable element, which attaches to the accelerometer-containing electronic circuitry/component 102 (and which may be designed as a single-use or reusable component) and is locked in place using a simple locking mechanism, such as an adhesive material, push-push type connector (e.g., 3M 7E50-0016-00, 3M, St. Paul, Minn.), push-pull connector (e.g., 3M 7G24), latching connector (e.g., Omnetics 0825, Omnetics Connector Corporation, Minneapolis, Minn.), Velcro, medical tape, plastic lock, wire, or soldered connection (solder joint). As shown in FIG. 1 the housing 101 can be formed into an envelope, with an opening (sheath) for sliding and locking the accelerometer-containing electronic circuitry 102. The shape and dimensions of the housing's opening are, preferably, designed to match those of the accelerometer-containing electronic circuitry 102 and its electronic-coupling element (e.g., cable, wire, or connector 103). The housing may also contain padding material (foam) 104 around the circuitry 102, which can be made, for example, from double-coated urethane foam tape with acrylic adhesive (such as 3M model 4008 or 4016) or double-sided polyethylene foam tape with acrylic or rubber adhesive (such as 3M model 4462W). When the measurements are finished, the electronic circuitry 102 can be pulled out of the envelope, and the membrane envelope can be discarded.

Alternatively, the modular sensor in FIG. 1 can be assembled by attaching two flexible membranes 101M1 to both sides of the self-adhesive material. In this configuration, the padding foam can be left exposed along the perimeter of the sensor's thin side and/or covered by another protective material.

The sensor of this invention can be also manufactured as a single piece, similar to disposable ECG and EMG sensors, such as 3M Red Dot Monitoring Electrode with Foam Tape and Sticky Gel.

Figure 1B:
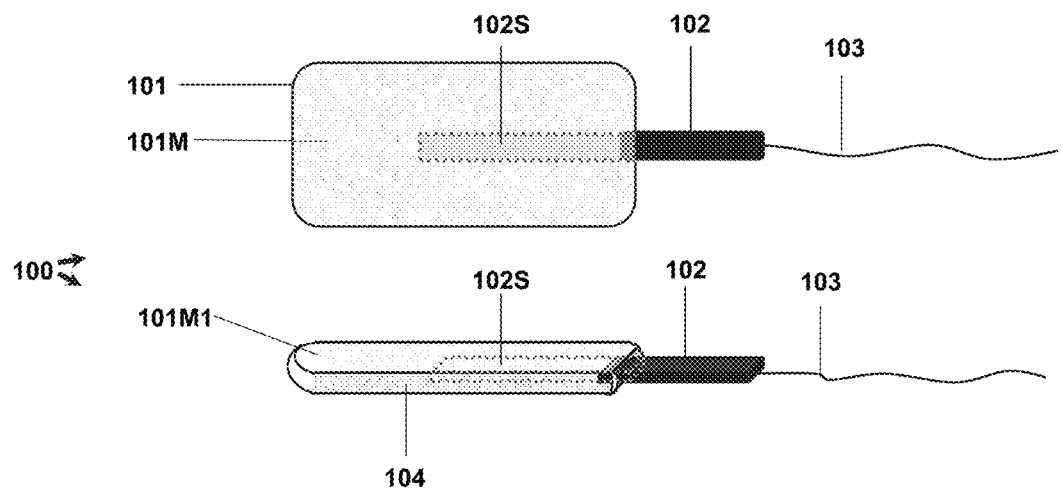

FIG. 1B shows an example process of connecting/disconnecting the housing 101 from the circuitry 102, using the slot (socket, pocket, shaft, or sheath) 102S, which is designed to fit the shape and dimensions of the circuitry 102. In FIG. 1B, the circuitry 102 is partially inserted (or extracted) from its slot 102S inside the housing 101.

Figure 1C:
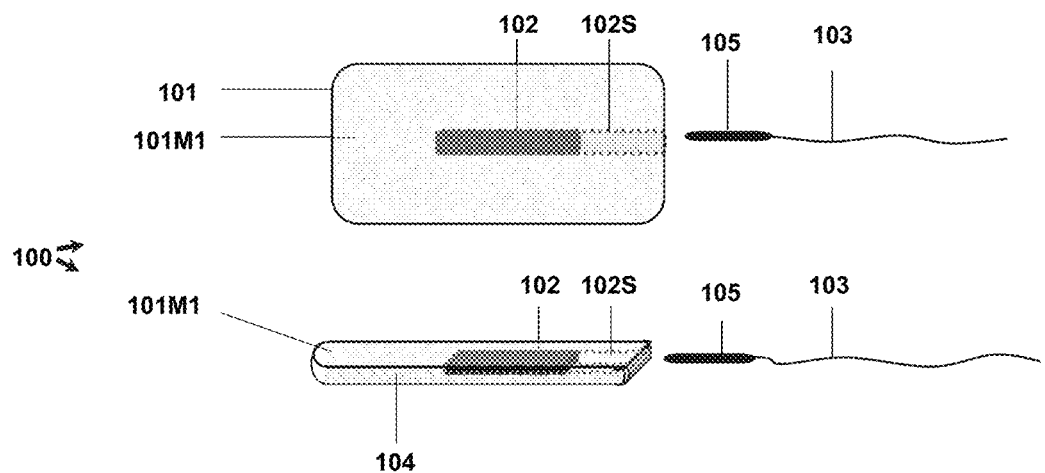

FIG. 1C shows another example process of connecting/disconnecting the housing 101 using a detachable cable (wire) 103 with a pin-type connector 105, which mates with a matching socket at the end of the circuitry 102.

Figure 1D:
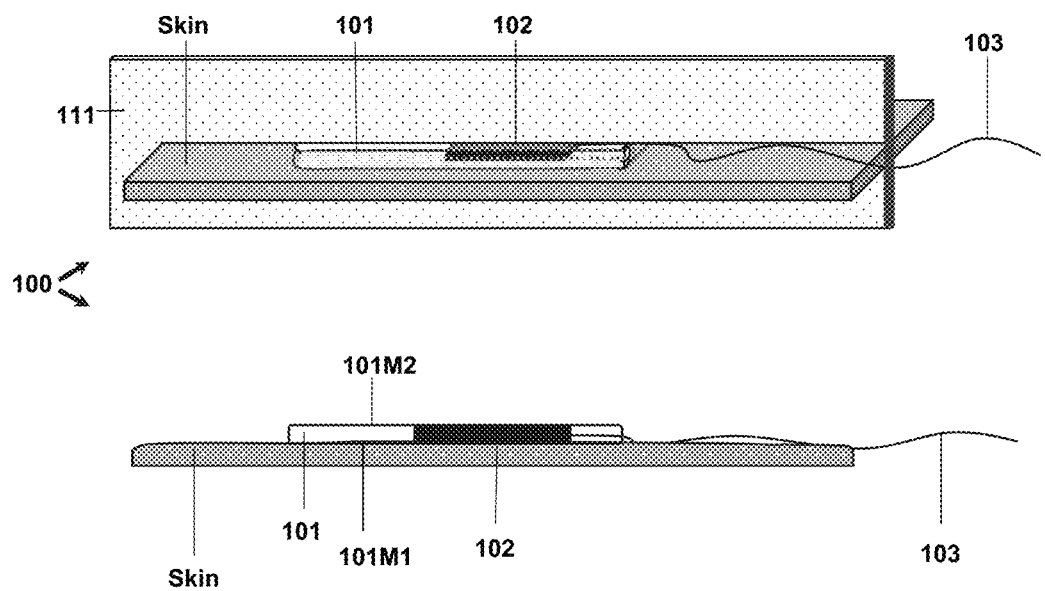

FIGS. 1D-E show cross-sections of example modular sensors 100 of this invention by plane 111. In FIG. 1D, the accelerometer-containing electronic circuitry 102 is tightly sandwiched between the skin-contacting conformal (flexible or stretchable) membrane 101M1 and the second conformal (flexible or stretchable) membrane 101M2. In this (preferable) configuration, the entire modular sensor 100 is very light and thin, and its movements, including movements of the accelerometer-containing electronic circuitry 102, follow the body-surface movements.

In FIG. 1E, the accelerometer-containing electronic circuitry 102 is in tight contact with or coupled to the skin-contacting conformal (flexible or stretchable) membrane 101M1 but separated (e.g., by free space or padding material) from the second membrane 101M2. Alternatively, the housing 101 may contain only one membrane 101M1, which provides contact with the skin surface. In this configuration, the entire sensor 100 may follow the skin-surface movements (vibrations), similar to the example shown in FIG. 1D.

However, in some configurations, the housing 101 may remain immovable (stationary); only the membrane 101M1 and accelerometer-containing electronic circuitry 102 (which is tightly coupled to the membrane 101M1) would follow the body-surface movements (vibrations). Thus it is important for the accelerometer-containing electronic circuitry 102 to be tightly coupled to either:

a. The membrane 101M1, which follows the body-surface movements (vibration); however, the movements may or may not be transmitted to (followed by) the rest of the housing 101, or b. The entire housing 101, which must follow the body-surface movements.

FIGS. 2A-B show two examples of circular modular sensors 200 of this invention, which contain the contact membrane (diaphragm) 201, the accelerometer-containing electronic component (circuitry) 202, and connecting cable (or wire) 203.

The modular sensor shown in FIG. 2B also contains a circular ECG/EMG electrode 204, which has an electrically conductive surface (made from metal, carbon, polymer, or other conductive material) and which is coupled to the skin surface using a conductive gel for recording ECG or EMG signals. In some embodiments, electrode 204 may have a circular snap connector on the top for connecting ECG or EMG leads (cables).

Alternatively, in some other embodiments, ECG/EMG signals can be transmitted to an acquisition module, along with accelerometer signals, using cable(s)/wire(s) 203. Thus, the sensor in FIG. 2B may register mechanical vibrations/accelerations, as well as electrical signals (ECG and/or EMG), using the circuitry 202. The circuitry 202 contains one or more accelerometers and may include other data-acquisition and processing functions (e.g., signal amplification and filtering) for the accelerometer signals, as well as for acquisition and processing of electrical (ECG and/or EMG) signals.

The housing 201 may be a disposable, single-use component, which may be attached to the skin using an electrically conductive gel or adhesive (such as those used for ECG and EMG recording). The housing 201 can be attached to the electronic circuitry/component 202 (which may be designed as a single-use or reusable component) using an adhesive or insertion-and-locking mechanism described in the specification with respect to housing 101 (FIG. 1), using an adhesive material, push-push type connector (e.g., 3M 7E50-0016-00), push-pull connector (e.g., 3M 7G24), latching connector (e.g., Omnetics 0825), Velcro, medical tape, or a plastic lock.

In some embodiments, other connector types can be also used with the sensors shown in FIG. 1 and FIG. 2. For example, a connecting wire (cable) 203 could be connected or disconnected from the sensor (which may be disposable) using a connecting pin at the cable end (e.g., pin-type connector 105 in FIG. 1C) which would fit into a mating socket at the end of the accelerometer-containing circuitry 202.

In some embodiments, the sensors shown in FIG. 1 and FIG. 2, including the housing (101 and 201), electronic circuitry (102 and 202), and cable/wiring (103 and 203), can be integrated into, embedded in, or attached to a flexible substrate described above. Such an integrated flexible sensor could be a single-use, disposable item.

Figure 3:
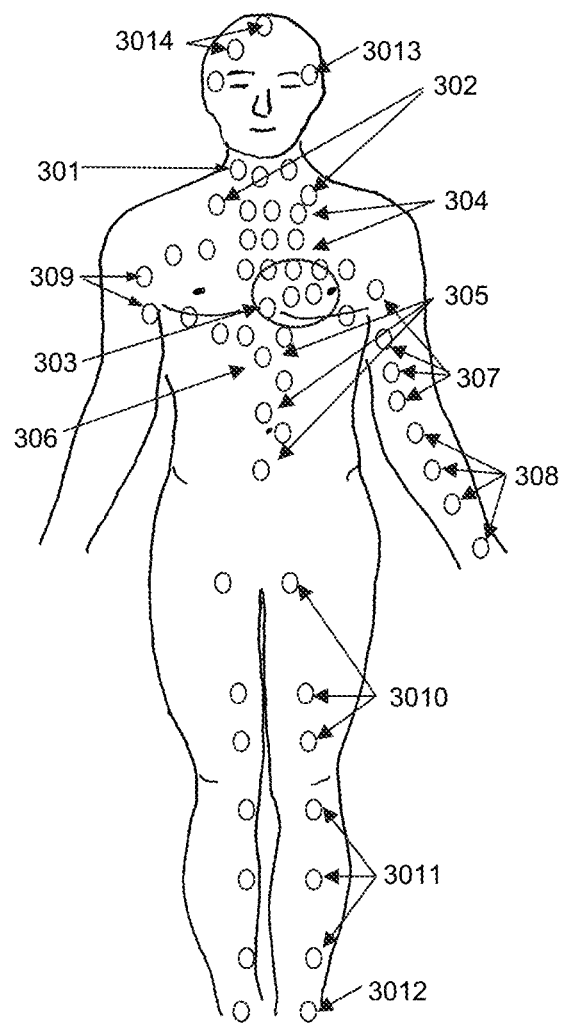
FIG. 3 is a drawing of examples of sensor locations on the body surface, including the torso, abdomen, neck, head, and upper and low limbs, for tracking cardiac forces and/or arterial blood-pressure waves.

FIG. 3 shows examples of sensor locations (which are marked by circles) for measuring (tracking) cardiac forces and/or arterial blood-pressure waves on the body surface, including the torso, abdomen, neck, head, and upper and lower limbs. The sensor locations may include the carotid arteries 301, subclavian arteries 302, precordial area 303, sternum and parasternal area 304, along the ascending and/or descending aorta, abdomen, and the abdominal aorta 305, subxiphoid area 306, upper limb and brachial artery 307, radial artery and wrist 308, axillary artery 309, lower limb and femoral artery 3010, anterior tibial artery 3011, foot, dorsalis pedis artery, and arch of foot artery 3012, head and temporal artery 3013, and its branches 3014.

Other possible sensor locations (not shown in FIG. 3) include the pulmonary artery, renal, and digital arteries. The sensor locations can be changed and optimized according to setting and application specifics, age, gender, medical history, diagnosis, blood vessels, or region of vascular tree being investigated.

Figures 4A, 4B:
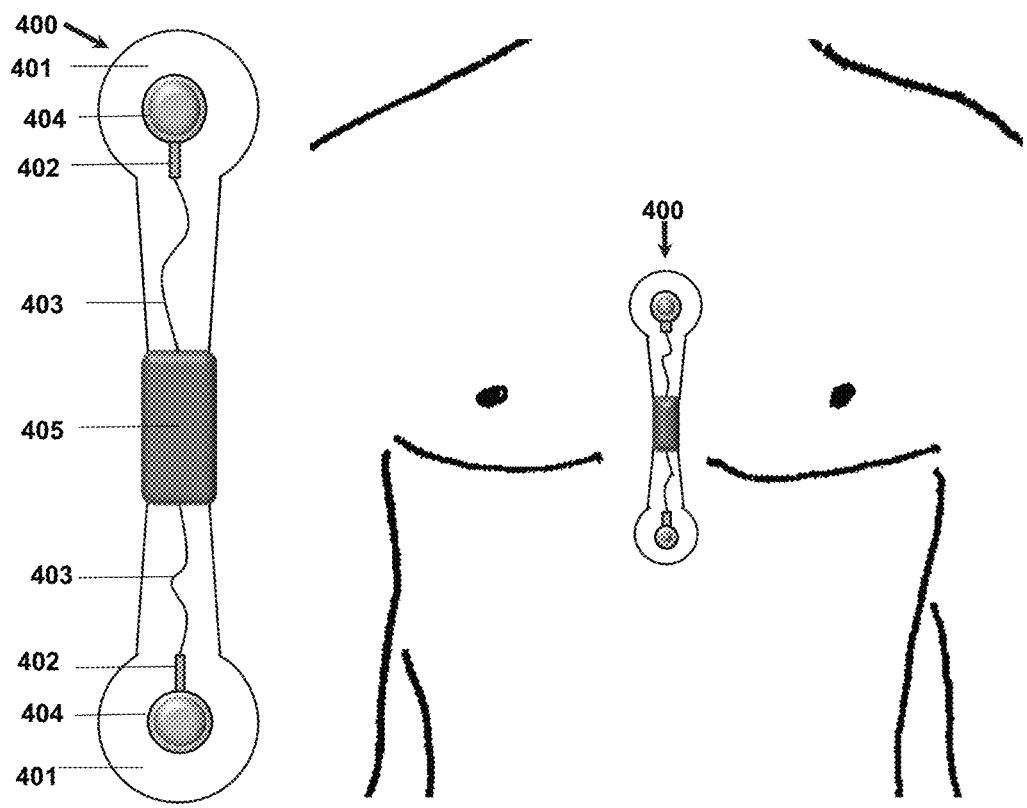

FIGS. 4A-B show an example patch sensor 400, which contains two modular sensors 401. Each modular sensor 401 contains accelerometer-containing circuitry (acquisition component/module) 402 for registering mechanical vibrations (movements, accelerations) indicative of cardiovascular, respiratory, and/or other activity, as well as ECG and/or EMG electrodes 404, which are electrically coupled to the skin surface using a conductive gel and/or adhesive material (e.g., a standard, disposable ECG and/or EMG electrode, such as 3M Red-Dot disposable ECG electrodes), and/or medical tape, to register electrophysiological activity (ECG and/or EMG). The accelerometer-containing elements 402 and electrodes 404 are connected to a central control module 405 via connecting cables (wires) 403. The central control module 405 may be covered by a plastic or metal enclosure, and may contain one or more components selected from the following list:
a. Preferably, one or more microprocessor, FPGA, or CPLD;
b. Preferably, one or more A/D converters;
c. Preferably, one or more wireless transmitters (e.g., Bluetooth radio, WiFi, or Zigbee);
d. Preferably, one or more storage units (non-volatile memory, e.g., EPROM, EEPROM, magnetoresistive RAM, ferroelectric RAM, polymer printed RAM, flash, removable MMC or micro SD card, and/or non-removable/integral memory module);
e. Preferably, one or more ports (e.g., micro USB port) and/or connector for connecting an external cable and communicating with an external unit (e.g., a smart phone).

The central control module 405 is electrically connected to the circuitry 402 to control the circuitry 402 and/or receive collected information (data, signals). In some embodiments, the central control module 405 also receives information (data, signals) from the electrodes (sensors) 404, which record electrophysiological activity (ECG and/or EMG).

In some embodiments, modular sensor 400 may be disposable in its entirety. In some embodiments, modular sensor 400 may be attached to an underlying, disposable substrate (membrane), acting as a buffer between the skin surface and non-disposable part, including one or more components selected from: the central control module 405, accelerometer-containing elements 402, and electrodes 404. In some embodiments, the central control module 405 may be detached from the rest of the sensor, for example, using one of the attachment/locking mechanisms described in FIG. 1 and FIG. 2.

FIG. 4B shows the placement of the modular sensor 400 on the torso surface along the sternum. We note that the vertical placement along the sternum (above the sternum or within 2 inches of the center of the sternum along the left or right side of the sternum) provides several advantages:
a. Provides good skin contact away from major muscle groups, thus minimizing noise and interference;
b. Improves convenience of wearing the sensor for both men and women;
c. Allows high-quality recording of ECG (or cardiac electrophysiological activity) as well as cardiovascular mechanical activity above and below the heart level. Estimating a delay between the two measurements provides reliable evaluation of cardiac forces and arterial blood-pressure wave in one or more central arteries, as disclosed in the parent-case documents.

FIGS. 4A-H show variations of the patch (integral, multicomponent, modular) sensors 400 of this invention. FIG. 4A shows an example sensor 400, which includes two electrophysiological (ECG and/or EMG) electrodes (sensors) 404 and two accelerometer-containing circuitry parts 402, which are attached to (embedded, integrated into) a flexible substrate 401, which is covered with adhesive material and attaches to the skin. FIG. 4B shows an example of placement of the sensor 400 on the surface of the torso, along the sternum.

Figures 4C, 4D:
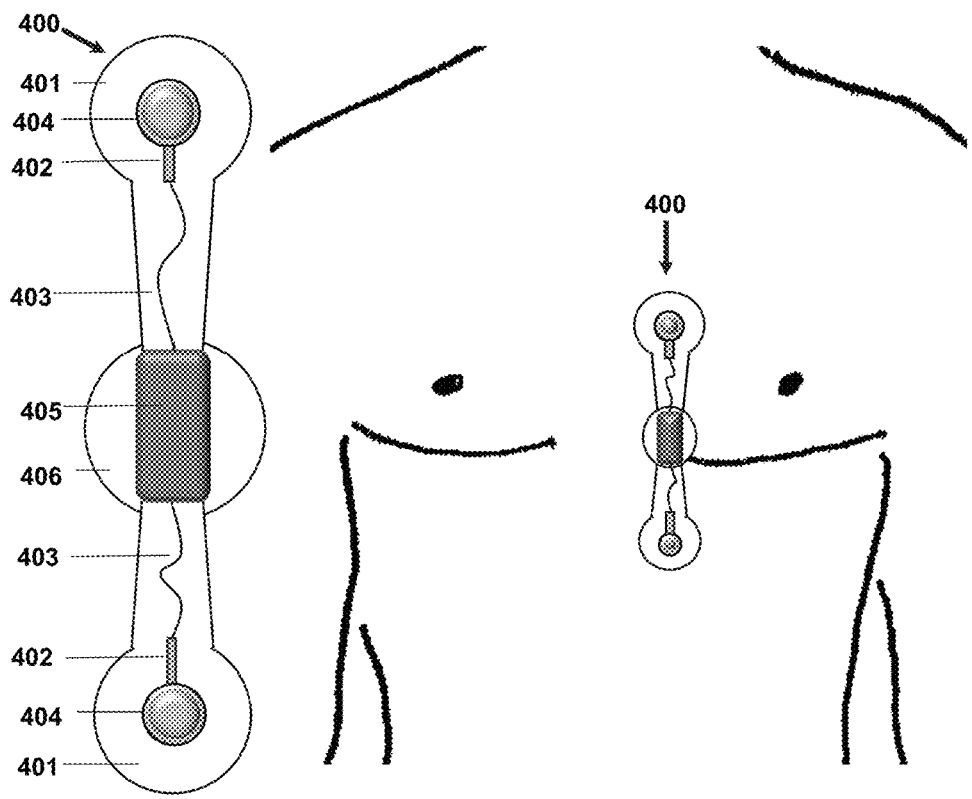

FIG. 4C shows an example modular sensor 400, which is similar to that in FIG. 4A and includes an extended, circular, skin-attachment (substrate) area 406 with adhesive material underneath the central control unit 405. FIG. 4D shows an example placement of the modular sensor 400 on the surface of the torso, along the left side of the sternum. Area 406 can be used for one or more of the following purposes:
a. Reinforcing the skin contact;
b. Sensing/registering electrophysiological activity (ECG or EMG) as the third electrode, in addition to the electrodes 404;

c. Sensing/registering mechanical activity using accelerometer-containing circuitry (vibrations, accelerations, motion), in addition to the analogous sensors with accelerometer-containing circuitry 402.

FIG. 4E shows an example modular sensor 400 in which the cables (wires) 403 that connect the circuitry 402 and electrophysiological sensors 404 with the central control unit 405 are free from the underlying substrate 401. This sensor design makes it easier to connect/disconnect the central control unit 405 from the sensor areas 401 (which may be disposable), using the locking mechanisms and connectors shown in FIG. 1 and detailed in its description. FIG. 4F shows example of placement of the sensor 400 on the surface of the torso, along the left side of the sternum.

Figures 4G, 4H:
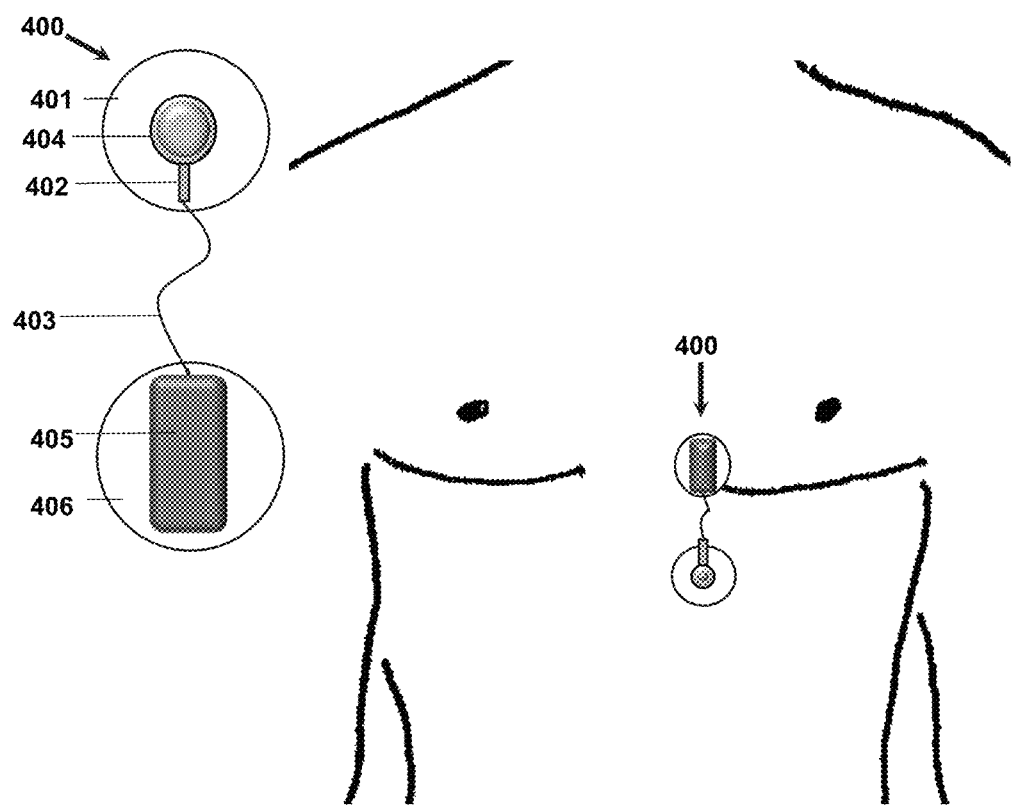

FIG. 4G shows an example modular sensor 400 which contains only one substrate area 401 (which is attached to the skin), circuitry 402, and an electrophysiological sensor 404 with the central control unit 405. The connecting cable (wire) 403, which connects the circuitry 402 and/or the electrophysiological sensor 404 with the central control unit 405, is free from the underlying substrate 401. This sensor design makes it easier to connect/disconnect the central control unit 405 from the sensor areas 401 (which may be disposable), using the locking mechanisms and connectors shown in FIG. 1 and detailed in its description. FIG. 4H shows example of placement of the sensor 400 on the surface of the torso, along the left side of the sternum.

Figure 5A:
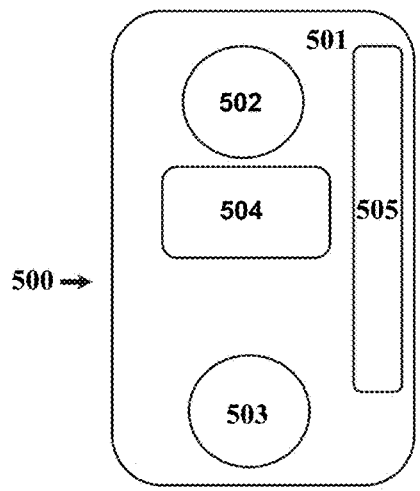
FIGS. 5A-D are diagrams of examples of integral sensor configurations containing two or more of the following elements: ECG electrodes, accelerometer(s), wireless transmitter, storage (memory) component, and communication component (port).

FIGS. 5A-D show variations of an integral sensor 500 of this invention. FIG. 5A is an example of an integral sensor 500, which contains flexible substrate 501, and the following components, which are embedded into or attached to the substrate: ECG electrodes 502 and 503, accelerometer-containing circuitry 504 for sensing mechanical accelerations/vibrations/motion, and a wireless transmitter 505 (e.g., Bluetooth, WiFi, Zigbee, or combination thereof).

Figure 5B:
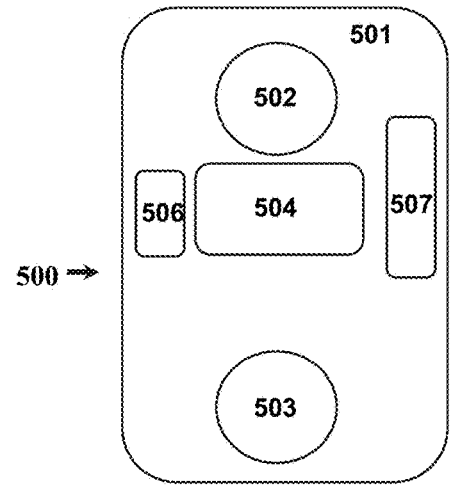

FIG. 5B is an example of an integral sensor 500, which contains flexible substrate 501, and the following components, which are embedded into or attached to the substrate: ECG electrodes 502 and 503, accelerometer-containing circuitry 504 for sensing mechanical accelerations/vibrations/motion, storage (memory) component 506, and communication component (e.g., a micro USB port) 507.

Figure 5C:
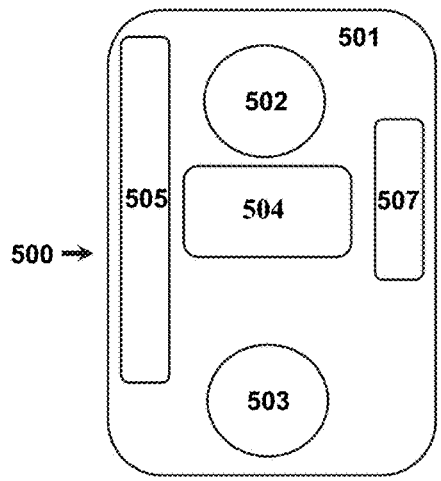

FIG. 5C is an example of an integral sensor 500, which contains flexible substrate 501, and the following components, which are embedded into or attached to the substrate: ECG electrodes 502 and 503, accelerometer-containing circuitry 504 for sensing mechanical accelerations/vibrations/motion, a wireless transmitter 505, and communication component (e.g., a micro USB port) 507.

Figure 5D:
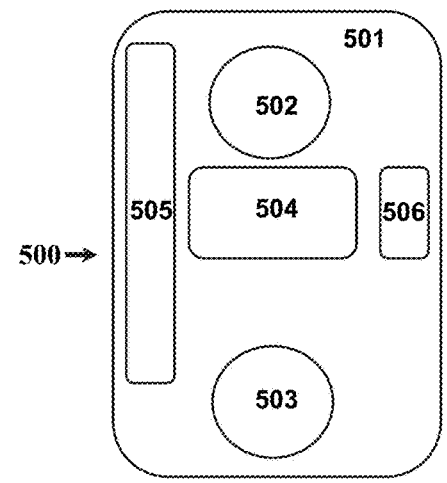

FIG. 5D is an example of an integral sensor 500, which contains flexible substrate 501, and the following components, which are embedded into or attached to the substrate: ECG electrodes 502 and 503, accelerometer-containing circuitry 504 for sensing mechanical accelerations/vibrations/motion, a wireless transmitter 505, and a storage (memory) component 506.

Figure 6A:
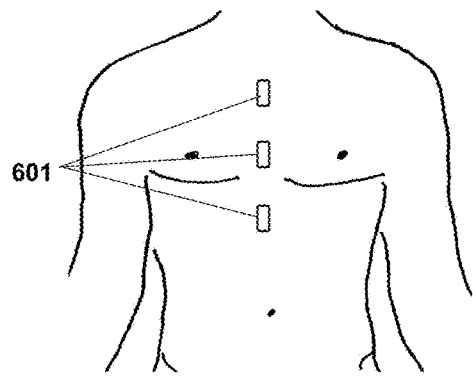
FIGS. 6A-F are drawings of examples of sensor placements on the torso surface.
Figure 6B:
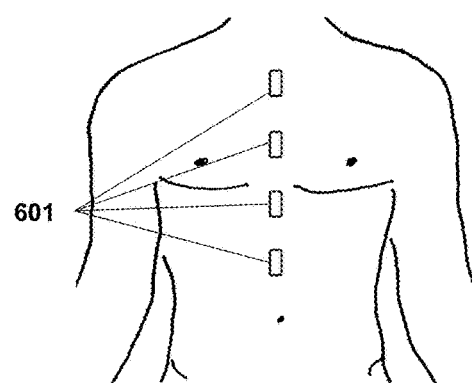
Figure 6C:
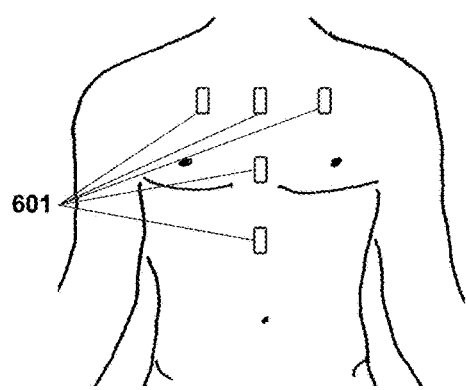
Figure 6D:
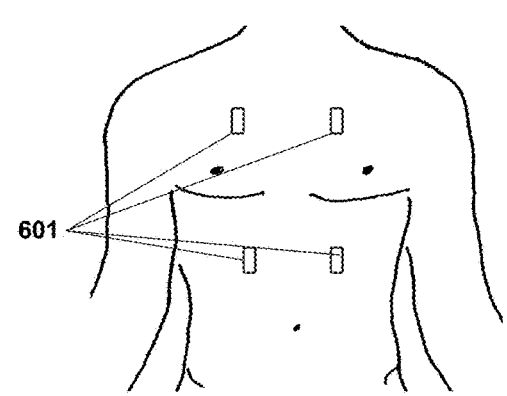
Figure 6E:
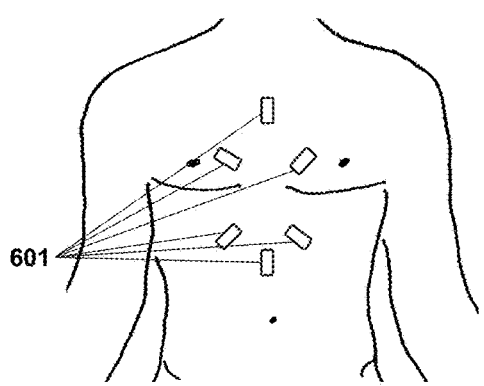
Figure 6F:
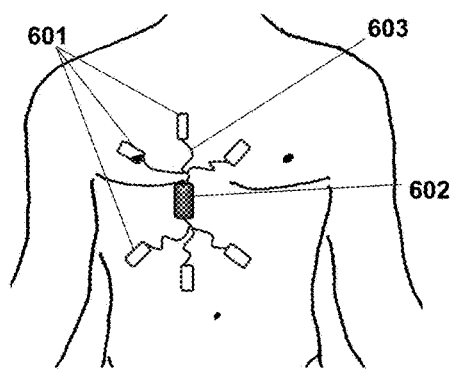

FIGS. 6A-F show example placements of the sensors of this invention (e.g., sensors shown in FIGS. 1-5) on the torso surface. FIG. 6A shows an example placement of three sensors 601 positioned vertically along the sternum. FIG. 6B shows an example placement of four sensors 601 positioned vertically along the sternum. FIG. 6C shows an example placement of five sensors 601; three sensors are positioned vertically along the sternum and two sensors are positioned on both sides of the sternum. FIG. 6D shows an example placement of four sensors 601 positioned symmetrically on both sides of the sternum. FIG. 6E shows an example placement of six sensors 601, which are arranged in a circle centered in mid-sternum. FIG. 6F shows an example placement of six sensors 601 centered around the sternum and connected to a central control unit 602 using connecting wires (cables) 603. The central control unit 602 receives information (data, signals) from all six sensors. Module 602 may contain a wireless transmission module (e.g., Bluetooth module) for transmitting received information to an external receiving module (e.g., smart phone). Module 602 may also contain a memory module for storing received data (e.g., a micro SD card), which may be removable or non-removable (integral). Module 602 may contain a micro USB port for connecting a cable and exchanging information with an external device. Module 602 may also contain other components and perform other control and processing functions as shown in FIGS. 1-5 and their descriptions above.

Figure 7A:
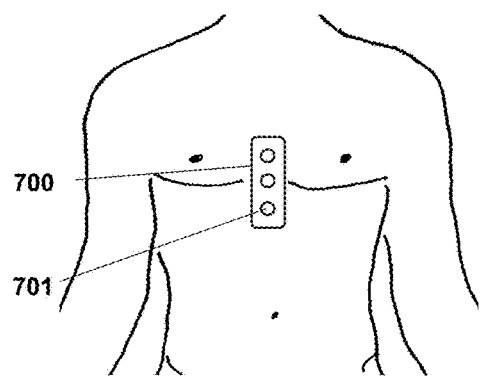
FIGS. 7A-F are drawings of example patches and their placements on the torso surface.
Figure 7B:
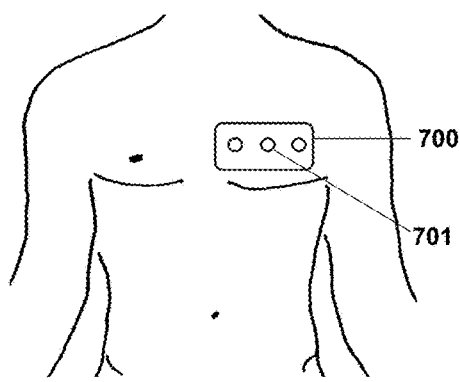
Figure 7C:
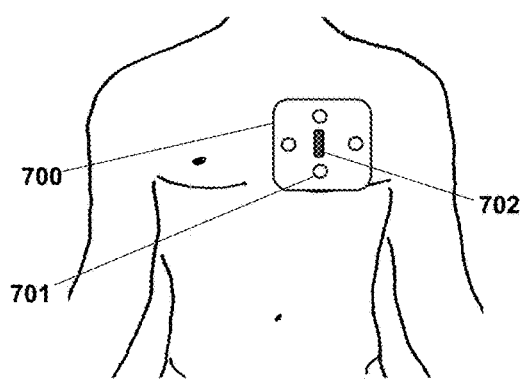
Figure 7D:
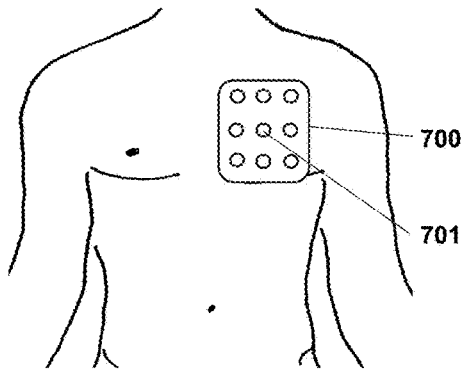
Figure 7E:
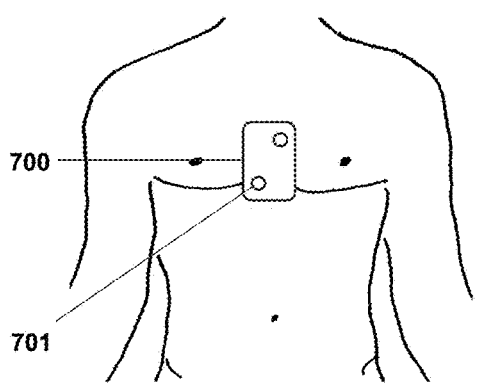
Figure 7F:
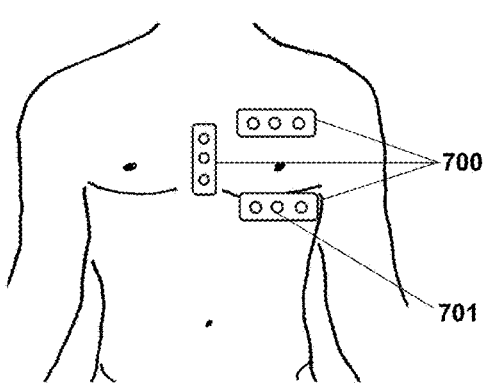
Figure 8A:
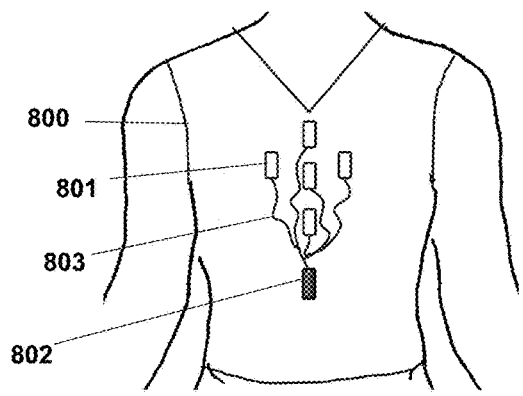
FIGS. 8A-E are drawings of example sensors and integrated sensor modules, which are attached to (integrated into) a vest.
Figure 8B:
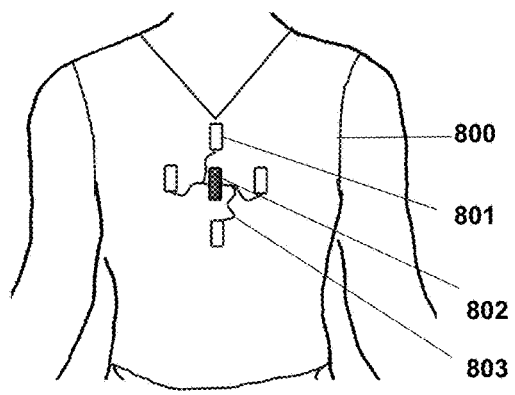
Figure 8C:
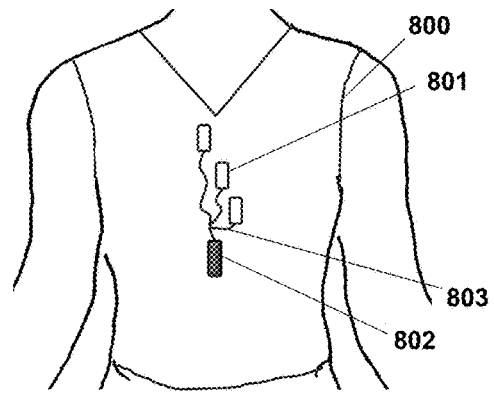
Figure 8D:
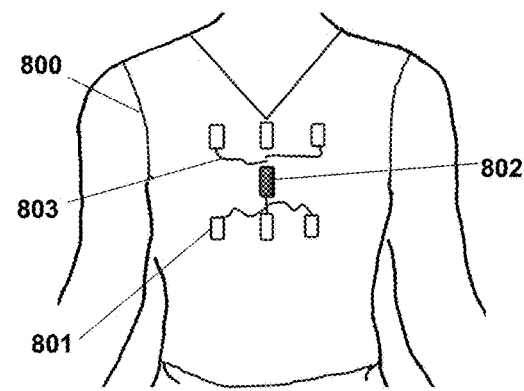
Figure 8E:
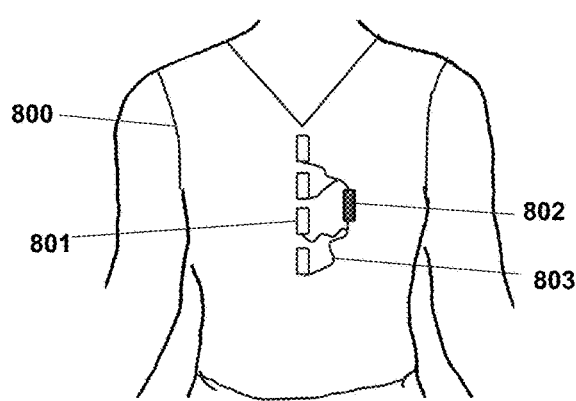

FIGS. 7A-F show example placements of the patch (integral) sensors 700 of this invention (e.g., sensors shown in FIGS. 1-5) on the torso surface. FIG. 7A shows example placement of a patch sensor 700 of this invention with three accelerometer-containing sensors 701 positioned vertically along the sternum. FIG. 7B shows example placement of a patch sensor 700 of this invention with three accelerometer-containing sensors 701 positioned horizontally in the precordial region. FIG. 7C shows example placement of a patch sensor 700 of this invention with four accelerometer-containing sensors 701 positioned in the precordial region. The sensor 700 also includes a central control unit 702. (The central control unit and its functions were described earlier in this specification with respect to sensors 400, 500, and 601 [FIGS. 4-6].) FIG. 7D shows example placement of a patch sensor 700 of this invention with six accelerometer-containing sensors 701 positioned in the precordial region. FIG. 7E shows example placement of a patch sensor 700 of this invention with two accelerometer-containing sensors 701 positioned diagonally in the sternal region. FIG. 7F shows example placement of three patch sensors 700 of this invention in the precordial region; each patch sensor includes three accelerometer-containing sensors 701.

FIG. 8 shows example sensors (e.g., sensors 100, 200, 400, 500) of this invention integrated into (attached to) a wearable west 800. FIG. 8A shows an example of sensor assembly, which consists of five sensors 801, which are connected to a central control unit 802. (The central control unit and its functions were described earlier in this specification with respect to sensors 400, 500, and 601 [FIGS. 4-6].) FIG. 8B shows an example of sensor assembly, which consists of four sensors 801, which are connected to a central control unit 802 using connecting wires (cables) 803. FIG. 8C shows an example of sensor assembly, which consists of three sensors 801, which are connected to a central control unit 802. FIG. 8D shows an example of sensor assembly, which consists of six sensors 801, which are connected to a central control unit 802. FIG. 8E shows an example of sensor assembly, which consists of four sensors 801, which are positioned along the sternum and connected to a central control unit 802.

FIGS. 9A-H show example KardiaSens sensors of this invention, which are connected to a central control unit 904. (The central control unit and its functions were described earlier in this specification with respect to sensors 400, 500, and 601 [FIGS. 4-6].) Unit 904 is attached to (or integrated into) a belt or a strap.

Figure 9A:
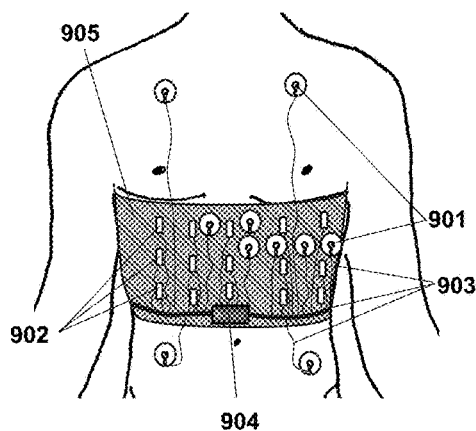
FIGS. 9A-H are drawings of example sensors, integrated sensor modules, and patch configurations, which include a strap and/or a belt, and the sensors' placements on the torso surface.
Figure 9B:
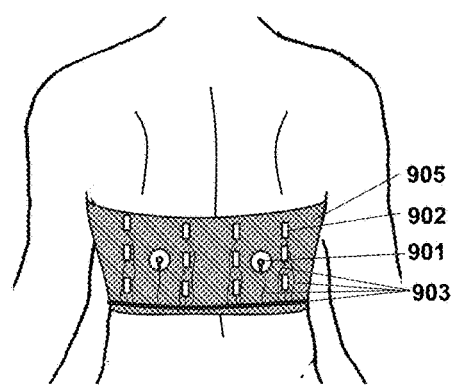

FIGS. 9A-B show front and back views of example KardiaSens sensors, some of which are embedded into (attached to, integrated into) a torso strap 905. In this example, the ECG measurement components 901 and the accelerometer-containing circuitry 902 for measuring mechanical movements of the torso surface are not necessarily integrated into a single sensor; instead, they may be located at different sites as shown in FIGS. 9A-B. The sensors 901 and 902 are connected to a central control unit 904 using connecting cables/wires 903.

Figure 9C:
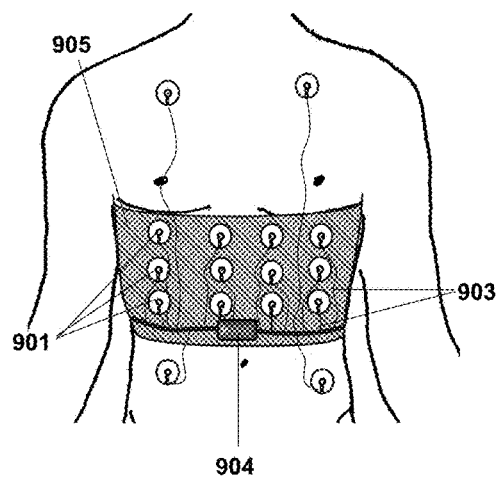
Figure 9D:
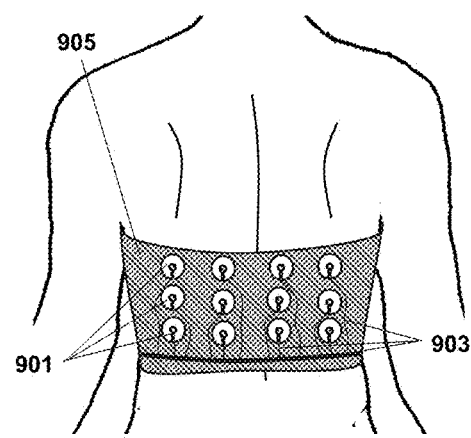

FIGS. 9C-D show similar frontal and back views of example KardiaSens sensors, some of which are embedded into (attached to, integrated into) a torso strap 905. However, in this example the ECG measurement component and the accelerometer-containing circuitry for measuring mechanical movements of the torso surface are integrated (combined) into sensors 901, which may be similar to sensor 200 in FIG. 2B. The sensors 901 are connected to a central control unit 904 using connecting cables (wires) 903.

Figure 9E:
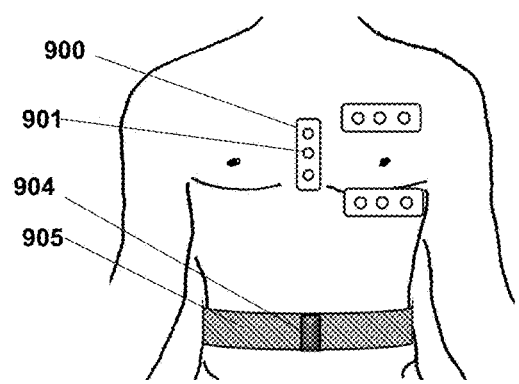

FIG. 9E shows an example of three integral patches 900; each patch sensor contains three accelerometer-containing sensors 901, which communicate wirelessly (e.g., using a Bluetooth or WiFi radio) with the central control unit 904. Unit 904 is attached to (integrated into) a waist belt 905. Unit 904 may control operation of the sensors 901 (e.g., power on/off, data-acquisition settings, including sampling rate, duration of the data recording, filter selection).

Figure 9F:
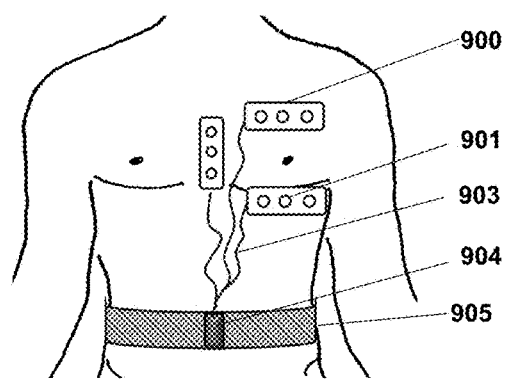

FIG. 9F shows an example of three integral patches 900; each patch sensor contains three accelerometer-containing sensors 901, which communicate (using connecting cables/wires 903) with the central control unit 904. Unit 904 is attached to (integrated into) a waist belt 905. Unit 904 may control operation of the sensors 901 (e.g., power on/off, data-acquisition settings, including sampling rate, duration of the data recording, filter selection).

Figure 9G:
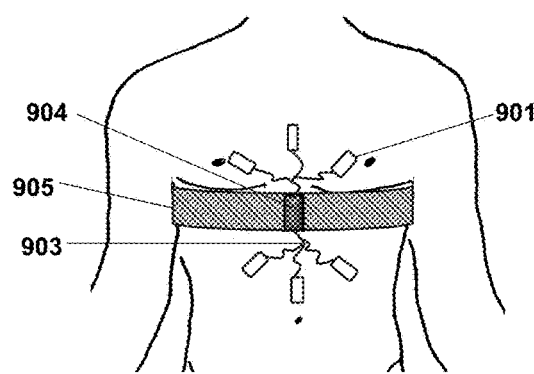

FIG. 9G shows example sensors 901, which communicate (using connecting cables/wires 903) with the central control unit 904. Unit 904 is attached to (integrated into) a chest strap 905. Unit 904 may control operation of the sensors 901 (e.g., power on/off, data-acquisition settings, including sampling rate, duration of the data recording, filter selection).

Figure 9H:
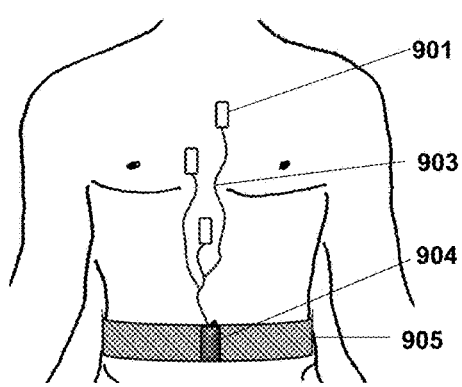

FIG. 9H shows example sensors 901, which communicate (using connecting cables/wires 903) with the central control unit 904. Unit 904 is attached to (integrated into) a waist belt 905. Unit 904 may control operation of the sensors 901 (e.g., power on/off, data-acquisition settings, including sampling rate, duration of the data recording, filter selection).

Figure 10A:
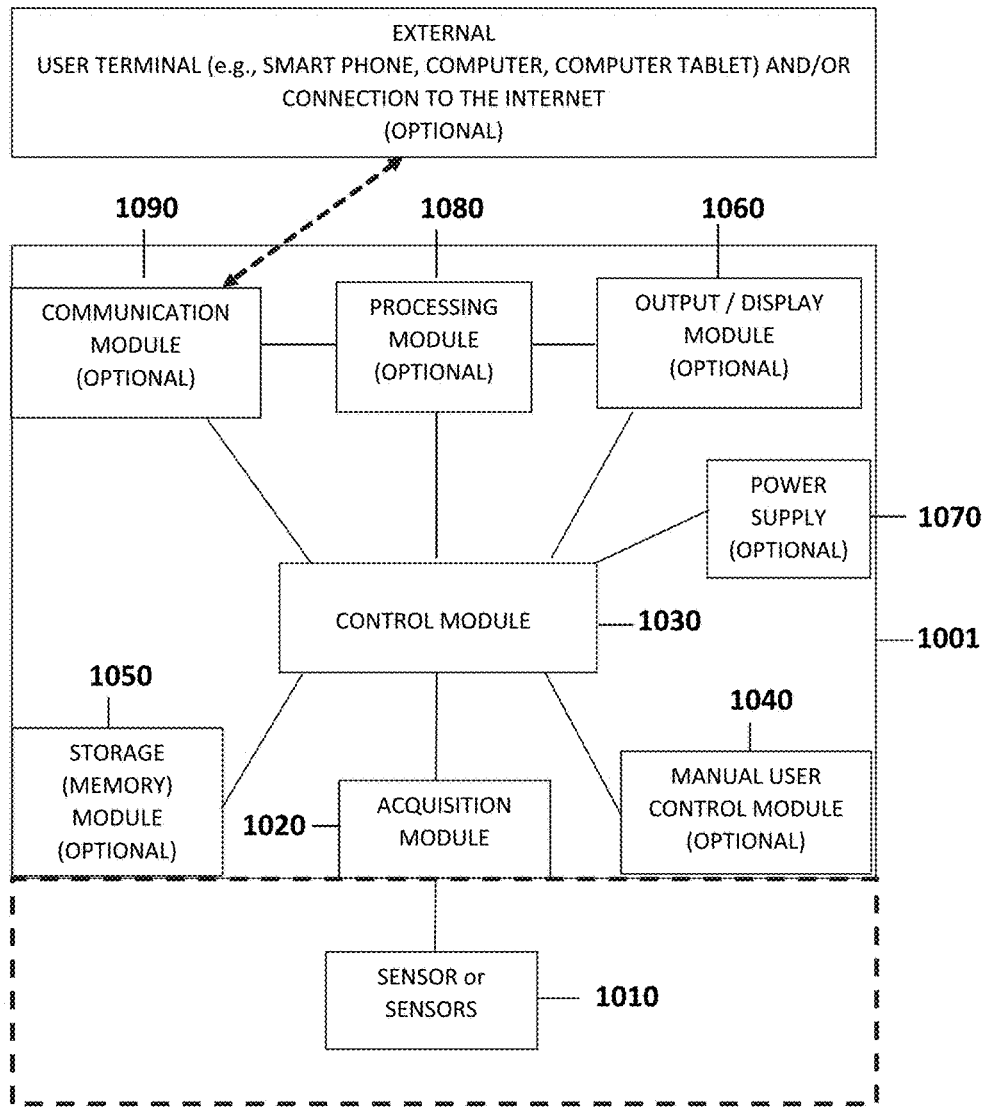
FIGS. 10A-C are block diagrams of some preferred embodiments of the system architecture that include: sensor(s), one or more acquisition modules (units), one or more control modules, one or more optional storage (memory) modules, one or more optional manual user-control modules, one or more power supplies, one or more optional communication modules, one or more optional processing modules, and one or more optional output/display modules. Note that all of the shown modules can be integrated into a single compact, mobile unit, which can also have one or more optional external user terminals (e.g., smart phone, computer, computer tablet) with one or more optional connections to the Internet. The user terminal provides a connection to the Internet server (cloud), which may also contain one or more processing modules.
Figure 10B:
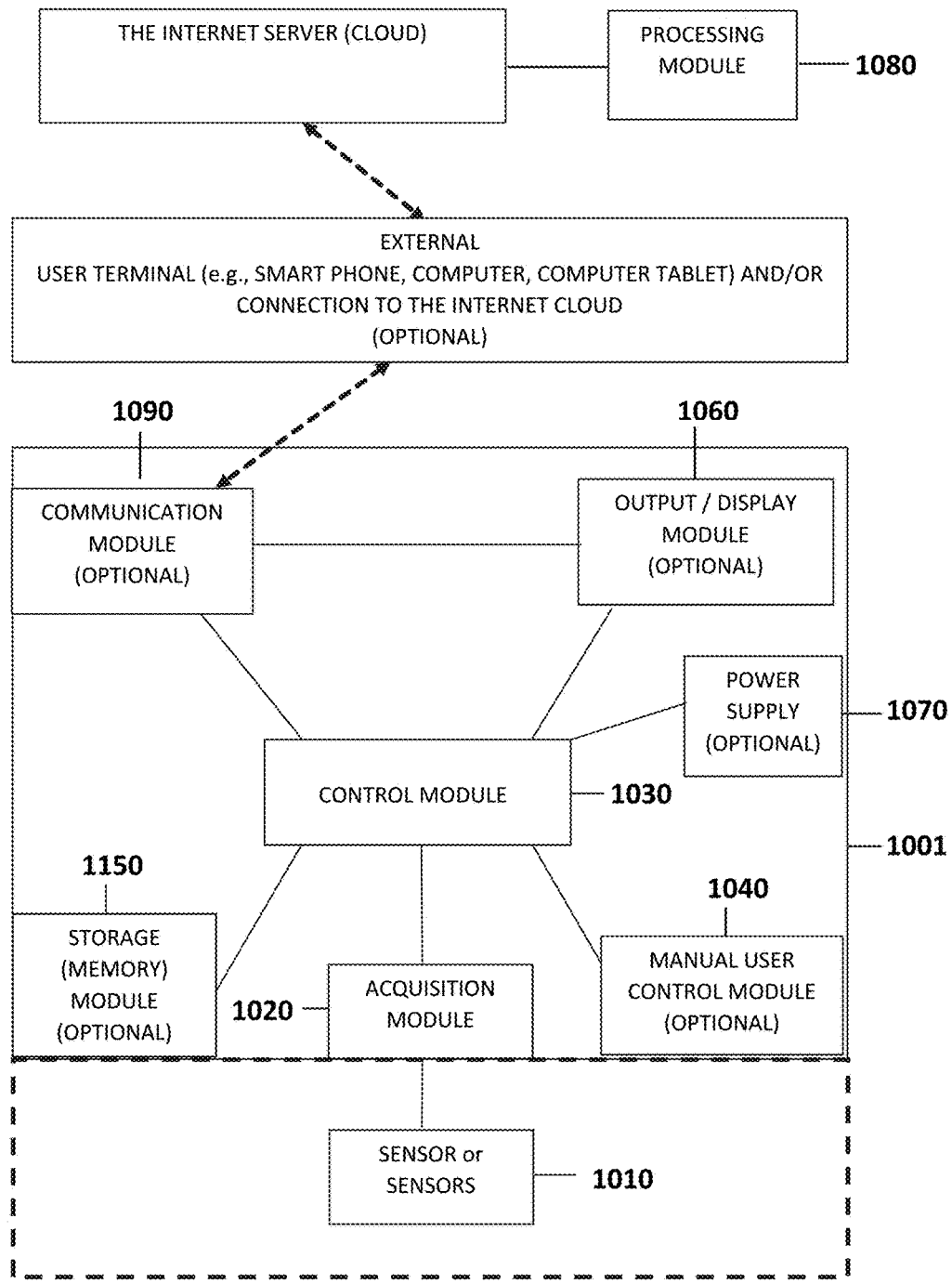
Figure 10C:
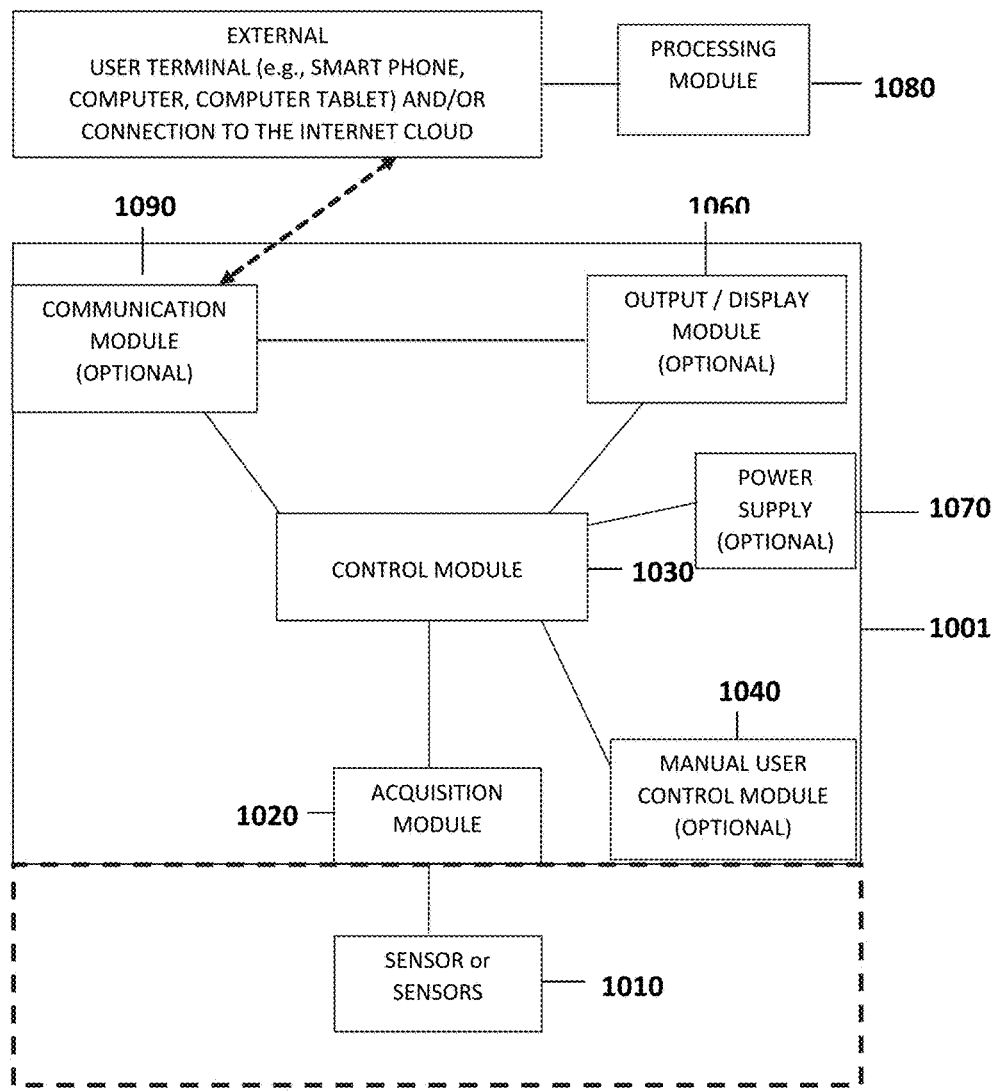

FIGS. 10A-C show three examples of the system architecture of this invention. The example systems in FIGS. 10A-C may include any of the sensors, integral sensors, and patches shown in FIGS. 1-9. The example systems of this invention shown in FIGS. 10A-C may be implemented as: one or more miniature, wearable patches (integral sensor); a collection (combination) of wearable patches (sensors); one or more wearable systems attached to (integrated into, embedded in) a wearable west; a wearable system with one or more central control units attached to a belt or strap; or a non-wearable (stationary) diagnostic and/or monitoring system, such as a bedside monitoring system or a standalone diagnostic system with one or more sensors (or sensor arrays), which are attached to the skin of the torso.

FIG. 10A is an example architecture of an integrated system/sensor/device 1001, which may be mounted/attached to an individual using an adhesive patch, chest strap, or waist belt, which may be connected to the sensors using cables/wires or a flexible substrate as described above, and which contains:

a. One or more sensors 1010 (described earlier in this specification with respect to sensors 101, 201, 301, 400, 500, 601 [FIGS. 1-6] and described in the parent-case documents), which may be integrated with the rest of the system (e.g., using a patch sensor) as described above, or connected to the rest of the system using cable(s), wire(s), or wireless communication (e.g., Bluetooth, WiFi, or Zigbee module);

b. One or more acquisition modules 1020, which may include an A/D converter as described above;

c. One or more control modules 1030, which may contain a microprocessor (e.g., MSP-430, Texas Instruments, Dallas, Tex.), FPGA (e.g., Spartan 7, Xilinx, Palo Alto, Calif.), or CPLD (Altera MAX 7000-series, Altera, Palo Alto, Calif.); the module controls the system operation through executable code/instructions (firmware or software), communicates with other modules, receives data from the acquisition module 1020, optionally performs data processing (e.g., filtering, averaging, and/or calibration), and sends the data to one or more optional modules selected from:

A. A manual user-control module 1040;
B. A storage module 1050;
C. An output/display module 1060;
D. A power-supply module 1070;
E. A processing module 1080;
F. A communication module 1090;

d. Preferably, one or more optional manual user-control modules 1040, which may include a button(s) or a touch screen providing an interface for a user to perform one or more of the following functions: turn the system on, initiate data transmission, mark the time of occurrence of an important event (e.g., cardiac arrhythmia, chest pain, or exercise), reprogram the settings (e.g., the thresholds for normal/abnormal heart rate, bradycardia, tachycardia, ECG patterns, normal/abnormal arterial blood pressure, normal/abnormal AP-wave speed in the central arteries);

e. Preferably, one or more optional storage modules 1050 (non-volatile memory, e.g., EPROM, EEPROM, magnetoresistive RAM, ferroelectric RAM, polymer printed RAM, flash, removable MMC or micro SD card, and/or non-removable/integral memory module) for storing the acquired data as well as executable instructions (e.g., initialization settings for the control module, such as the recording duration, sampling rate, number of channels of data, data averaging, calibration, and/or processing), wherein the executable instructions may be pre-programmed or received from an external device via the communication module 1090;

f. Preferably, one or more optional output/display modules 1060, which may include light-emitting diodes (LED) or a liquid crystal display (LCD) to indicate that:
A. The system is turned on;
B. The recording has started or stopped;
C. Signal quality is acceptable or unacceptable;
D. Physiological changes are encountered;
E. User-logged event has occurred;
F. A transmission link with an external device (user terminal) is established;
G. Data transmission with an external device has started;

g. Preferably, one or more power supply 1070, which may include a lithium-ion battery, such as a lithium cobalt oxide, lithium iron phosphate, lithium ion manganese oxide, lithium nickel manganese cobalt oxide, lithium nickel cobalt aluminum oxide, lithium titanate, or lithium-sulfur battery, a lithium battery, or a solar battery;

h. Preferably, one or more optional processing modules 1080, which may perform one or more processing steps selected from:
   A. Calibrating the data;
   B. Estimating signal quality;
   C. Time averaging (i.e., averaging the data over multiple cardiac cycles) and/or averaging of data from different locations on the body surface;
   D. Computing a median sample;
   E. Computing heart rate;
   F. Computing the speed (velocity) of the pressure wave;
   G. Computing the PAT of the AP wave (the time interval between a specific ECG peak and a specific feature or peak of the torso-surface acceleration associated with the cardiac forces (BCG) and/or propagating AP wave, or a peak of the BCG jerk, or a combination thereof);
   H. Computing PTT (the time interval between the occurrence of a specific BCG peak, the $1^{st}$ time derivative of a specific BCG peak, or a combination thereof, registered at different body-surface locations);
   I. Computing one or more amplitudes of one or more ECG or BCG peaks; and
   J. Computing respiratory rate;
i. Preferably, one or more optional communication modules 1090, which may include:
   A. A port for cable connection (e.g., a micro USB port); or
   B. A wireless-communication module (e.g., Bluetooth, WiFi, or Zigbee);
j. Preferably, one or more optional external user terminals (e.g., smart phone, computer, computer tablet), which communicates with the system 1001 via the communication module 1090 and performs one or more operations from the following list:
   A. Provides wireless or cable-based connection for transmitting the recorded data into a repository on the Internet server (cloud);
   B. Transmits the data to a healthcare professional via a phone line, wireless phone line, or the Internet;
   C. Performs data processing and/or analysis, including one or more operations selected from: time averaging, averaging of data from different sensors, computing a median sample, calibrating the data, estimating signal quality, computing heart rate, computing the speed of the AP wave, computing the time interval between an ECG peak and a BCG peak (or a peak of the BCG jerk), computing one or more amplitudes of one or more ECG or BCG peaks, and computing respiratory rate;
   D. Displays the data and/or results of data analysis.

FIG. 10B shows an example system architecture, which is similar to that in FIG. 10A. However, in FIG. 10B, the system 1001 does not include a storage module or processing module; instead, the processing is performed on the Internet server (cloud) using a remote processing module 1080.

FIG. 10C shows an example system 1001, which is similar to that in FIG. 10A but does not include a storage module or processing module. Instead, processing is performed on the external user terminal (e.g., smart phone, computer, or computer tablet) using a remote processing module 1080.

FIG. 11 shows photographs of the prototype system of this invention. FIGS. 11A-B show a prototype KardiaSens sensor 1100 of this invention (profile and top views, respectively). In particular, FIG. 11B shows the housing 1101 and accelerometer-containing electronic circuitry 1102, which is covered by its own protective housing, and electronic-coupling element (cable) 1103.

FIG. 11C shows a photograph of the prototype sensors 1101 attached to the skin of a torso of a human subject. FIG. 11D shows a computer screenshot from a program that acquires, processes, and displays data (signals) obtained from the KardiaSens sensors 1101 placed on the torso surface as shown in FIG. 11C. For each sensor 1101, the raw acceleration signals (a, b, c) were processed (amplified and band-pass filtered) to remove low-frequency components (baseline wander and respiratory variations) and high-frequency noise (due to muscle contraction, movement, and system noise) and recorded at 2.5 kHz sampling rate. FIG. 11D, plots P1-P6, show the torso acceleration's vector magnitude $$M=\sqrt{a^2+b^2+c^2} \tag{1}$$

computed from the acceleration signals (a, b, c) along the three orthogonal axes (x, y, z) for each sensor 1101. Note the sharp deflections (peaks) generated by the cardiac forces (cardiac mechanical/contractile activity) and by the passage of arterial blood-pressure waves in the vicinity of each sensor. Plot P7 shows simultaneously recorded peripheral blood pressure from a reference oscillometric device (Ohmeda Finapres 2300, Finapres Medical Systems, Enschede, The Netherlands). Plot P8 shows simultaneous ECG recording. Plot P9 shows a time-averaged waveform of the signal M obtained from one of the KardiaSens sensors. Plots P10-P12 show graphs of the time differences (PTT) between the largest (dominant) peaks in plots P1-P6. This time is inversely proportional to the pressure-wave velocity (PWV). Tracking PWV and other parameters of the acceleration waveforms (P1-P6) allows computation of the AP as described in the parent-case documents, which are incorporated herein by reference.

Note that the dominant peaks in each sensor's data were detected using the time of the ECG R peak as reference. To improve the signal-to-noise ratio, the signals may be time-averaged by time-aligning the KardiaSens data obtained over >1 cardiac cycle, relative to the ECG R peak, which served as the fiducial point (reference) for the alignment. To improve the accuracy of peak detection, the $1^{st}$ time derivative of the acceleration signals (jerk) may be also used.

Figures 12A, 12B, 12C:
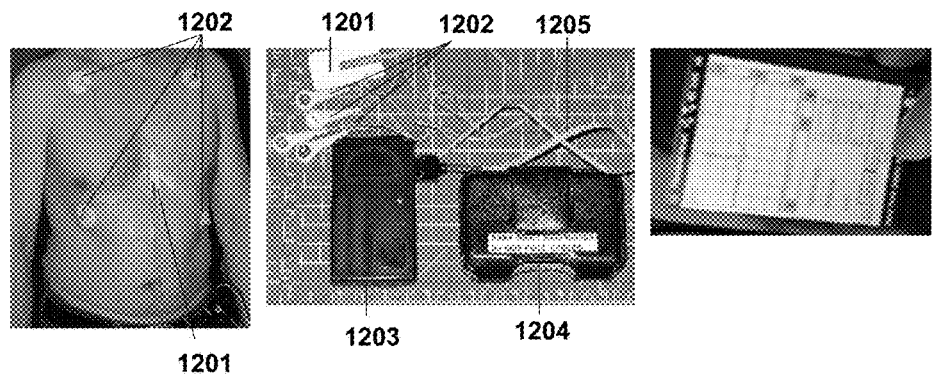
FIGS. 12A-D are a selection of photographs and data samples obtained from a human subject during ambulatory (overnight) monitoring using a portable (wearable, ambulatory, Holter, sleep-study) version of the system of this invention. The photographs include.

FIGS. 12A-C are photographs of a portable prototype of the system of this invention, which may be used for ambulatory monitoring (including nighttime monitoring and sleep study). FIG. 12A shows a reduced set of the KardiaSens sensors 1201 (centered in the region of the sternum, parasternal, and subxiphoid area) and ECG sensors 1202, which may be used for ambulatory monitoring of cardiac forces and AP in the central arteries. FIG. 12B shows the portable prototype system, including the central control unit 1203 with its wearable pouch 1204 (which may be clipped to a belt or clothing or placed in a pocket), the KardiaSens sensor 1201, and the ECG sensors 1202. The sensors are connected to the central control unit 1203 using connecting cables 1205. The central control unit 1203 may include data storage (memory), which may be a removable (e.g., micro SD card) or non-removable (integral) part of the unit 1203. The central control unit 1203 may also include a wireless-communication module (e.g., Bluetooth radio) for exchanging information with an external user terminal (EUT; e.g., smart phone, computer, Internet server/cloud, or computer tablet), as shown in FIG. 12C. The EUT runs a software application (program), which may include the following functions:

a. Controlling the central control unit 1203 by sending commands (e.g., to start/stop data recording) and settings (e.g., duration of data acquisition, number of channels, processing parameters, sampling rates) to the unit via a wireless link;

b. Receiving data from the central control unit 1203 via a wireless link;

c. Processing/analyzing data received from the central control unit 1203;

d. Displaying data received from the central control unit 1203;

e. Displaying results of data processing/analysis (e.g., heart rate, arterial blood pressure, changes in the cardiac forces, and/or their distribution), recommendations/advice, and/or biofeedback information;

f. Forwarding data, results of data processing/analysis, warnings, and/or recommendations to medical professionals via a wireless link (e.g., cell phone transmission) or cable connection (e.g., Ethernet connection).

Figure 12D:
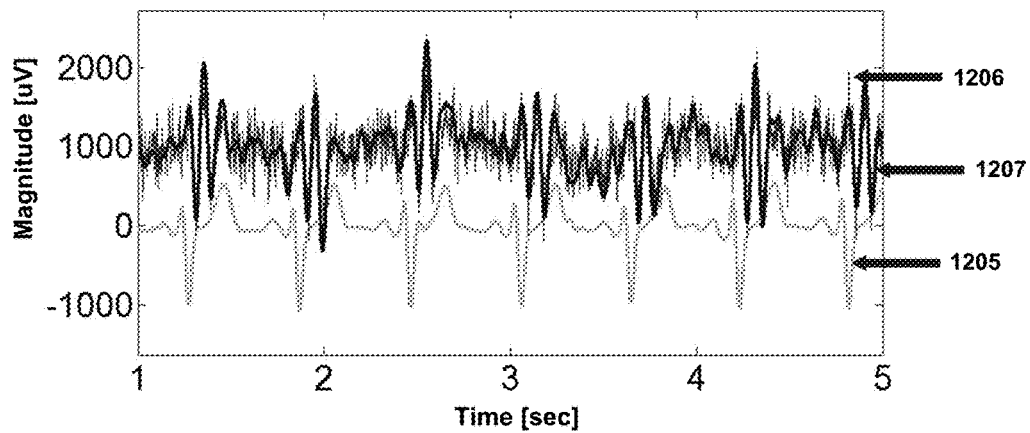

FIG. 12D shows an example of data acquired during overnight ambulatory monitoring using the system shown in FIGS. 12A-C. The data include ECG (lead II) 1205, the unprocessed torso-surface acceleration signal 1206 obtained using the sensor 1201, and the processed (band-pass filtered) signal 1206 (signal 1207) without low-frequency components (baseline wander, respiration) and high-frequency noise (muscle artifacts, movements, system noise, and ambient noise), which were removed by filtering.

Figure 13:
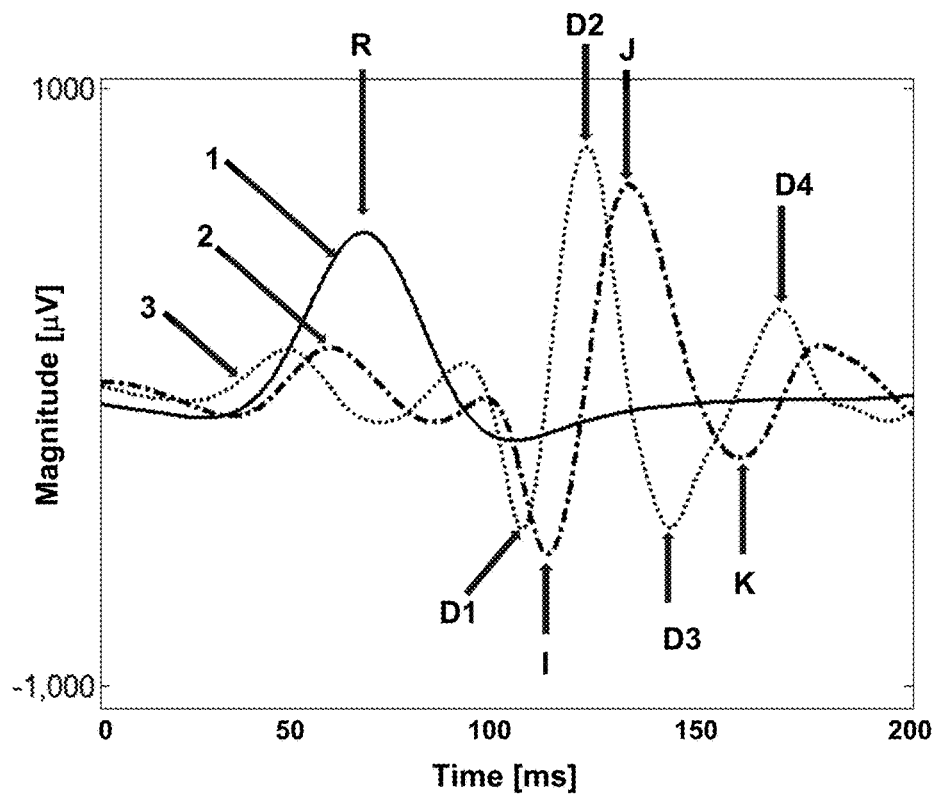
FIG. 13 is a selection of example signals registered simultaneously by the sensor and system of this invention, including ECG, acceleration of the torso surface caused by the cardiac forces, and the $1^{st}$ derivative of the torso-surface acceleration with respect to time (also referred to as the rate of change of acceleration, jerk, jolt, surge, or lurch).

FIG. 13 shows an example of simultaneously recorded data using the system of this invention. To increase the signal-to-noise ratio (signal quality), the data may be processed, including band-pass filtering (as described above) and/or signal averaging over multiple cardiac cycles using the ECG R peak as a reference point for the time alignment. FIG. 13 shows:

a. An ECG signal 1, including the R peak, which is often used as a reference (fiducial point) for time alignment, signal averaging over several cardiac cycles to improve signal-to-noise ratio, and/or for determining the time interval for detection of the torso-surface accelerations associated with cardiac forces;

b. The vector magnitude (M) signal 2 of the torso-surface acceleration obtained as described above, using a KardiaSens sensor; the signal includes its main peaks (I, J, K), which are used for tracking cardiac forces and/or AP in the central arteries, as described in the parent-case documents, which are incorporated herein by reference;

c. The $1^{st}$ time derivative (jerk) of the torso-surface acceleration 3; the signal includes its main peaks (D1, F2, D3, D4), which may be used for detecting and tracking the precise location of the peaks in the torso-surface acceleration signals (e.g., signal 2);

The peaks of the ECG signal and the peaks of the torso-surface acceleration (and its $1^{st}$ time derivative or jerk) signals acquired by KardiaSens sensors shown in FIG. 13 may be used by the system of this invention to evaluate the cardiac forces and AP in the central arteries, as described in the parent-case documents, which are incorporated herein by reference. The intervals between the time of occurrence of these peaks registered by different KardiaSens sensors may be used for tracking the distribution of cardiac forces on the torso surface and the passage of AP waves, as described in the parent-case documents, which are incorporated herein by reference.

Figure 14A:
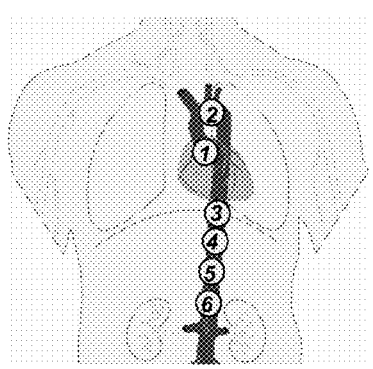
FIGS. 14A-B are a drawing of example sensor locations on the surface of the torso and a selection of ECG and accelerometer-registered signals, which were simultaneously recorded from some of the shown torso locations. (Torso and aorta drawing by Edoarado—Own work based on: Arterial System en.svg, Coronary arteries.svg., CC BY-SA 3.0, https://commons.wikimedia.org/w/index.php?curid=18231817.)
Figure 14B:
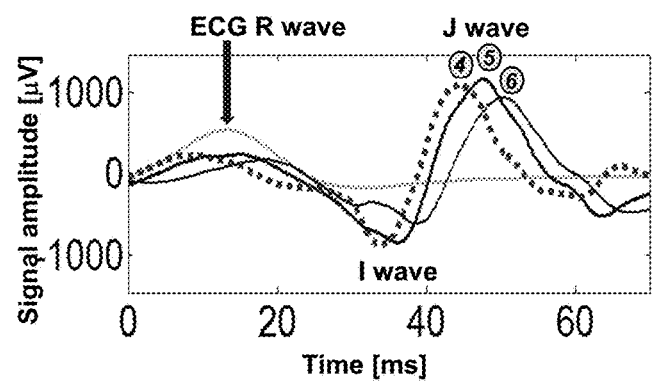

FIG. 14 shows examples of the KardiaSens sensors' locations and acquired data. FIG. 14A shows locations of the KardiaSens sensors (circles). Sensor 1 was placed at the root of the aorta; this sensor was used to detect the onset of the cardiac contraction. Sensors 2-6 were used to measure the AP-wave passage along the aorta. FIG. 14B shows an example of simultaneously obtained data from the KardiaSens sensors 4-6 in one experiment. The signals were processed as described above. The negative I wave represents the initial headward pressure force generated by the heart's movement and contraction at the beginning of systole, which includes isometric contraction and the onset of blood ejection, when the AP wavefront exits the left ventricle of the heart and enters the ascending aorta. The positive J wave represents subsequent footward force of the AP-wave movement from the aortic arch toward the descending and abdominal aorta. Thus, the time interval between the I and J waves corresponds to the AP-wave transit time along the aorta.

FIG. 15 shows examples of the locations of KardiaSens sensors on the torso surface and the data acquired from those sensors. FIG. 15A shows three sensor locations: mid-sternum (site 1), carotid artery on the neck (site 2), and mid-abdominal region (site 3). FIG. 15B shows examples of the KardiaSens signals 1501 collected from the three locations shown in FIG. 15A, as well as the simultaneously recorded ECG signal 1502 (which is superimposed over signals 1501). The signals were recorded at rest and during handgrip.

FIG. 15B also shows PTT, i.e., the time interval between the dominant (largest) peak of the torso-surface accelerations (BCG) registered by the KardiaSens sensors at the different body-surface locations shown in the figure. The panels were synchronized by the time of the ECG R peaks to show a shift in time of occurrence (relative delay) of the dominant (largest) peak of the KardiaSens signal at different levels of AP (which are shown in the bottom-right section of each panel). The figure also shows changes in the magnitude of the dominant peak of the KardiaSens signal at different levels of AP. The relationship (relative delays) between the time of occurrence of various peaks of the KardiaSens signals at different sensor locations and AP may be used by the system of this invention for monitoring (tracking) AP in the central arteries as described above. In addition, the relationship (relative delays) between the time of occurrence of various peaks of the KardiaSens signals at different sensor locations as well as the magnitudes of various peaks of the KardiaSens signals at different sensor locations may be used by the system of this invention to determine the distribution of cardiac forces on the torso surface as described above.

Dividing the distance traveled by the pressure wave (e.g., from the left ventricle to the KardiaSens sensor's location) by PTT yields the PWV. This speed is directly proportional to AP, because the pressure wave travels faster when the pressure increases. However, PWV is also affected by vascular stiffness; it increases when arterial walls become stiffer (less elastic). The changes in arterial stiffness are highly variable in peripheral arteries (e.g., in the finger arteries), and this variability represents a major obstacle in the derivation of AP using the measurements obtained from peripheral arteries, as disclosed in the parent-case documents, which are incorporated herein by reference. However, as further disclosed in the parent-case documents, the arterial stiffness is essentially unchanged (constant) in the aorta and large vessels, which allows the derivation and tracking of changes in AP from the pressure wave's amplitude and PTT measurements obtained in the large vessels. As FIG. 15B demonstrates, PTT becomes shorter (i.e., PWV increases) when systemic AP increases due to handgrip compared to rest (105/65 to 135/95 mm Hg). PAT (which is similar to PTT) was measured between the peak of the ECG R wave and the peak of the pressure wave in the abdominal aorta, as measured by a KardiaSens sensor positioned at Site 3 in FIG. 15A.

Figure 16:
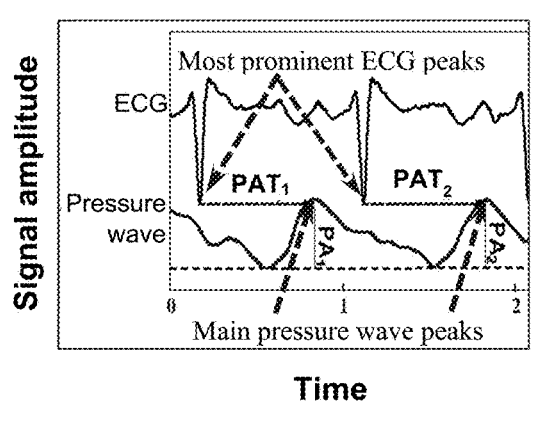
FIG. 16 is an example of ECG and pressure-wave signals and the detection of peaks in ECG and pressure-wave signals, as well as measurement of the pressure-wave amplitude (PA), PAT, and PTT using the two signals.

FIG. 16 shows examples of ECG and the AP-wave signals. The AP-wave signals were obtained by the time-integration of the torso-surface acceleration signals (i.e., the areas under the curve) registered by the KardiaSens sensors located in the vicinity of the aorta and radial artery. In addition, FIG. 16 show examples of some parameters extracted from the pressure-wave signals, including:

a. PAT, measured as the time interval between the most prominent ECG peak and the peak of the passing pressure wave (this PAT interval includes the pre-ejection period and PTT); the dominant peak of the pressure-wave signal was registered by the accelerometer-containing KardiaSens sensor when the pressure wave reached the sensor location;

b. PA, measured as the amplitude difference between the maximum and minimum of the AP wave.

Figure 17:
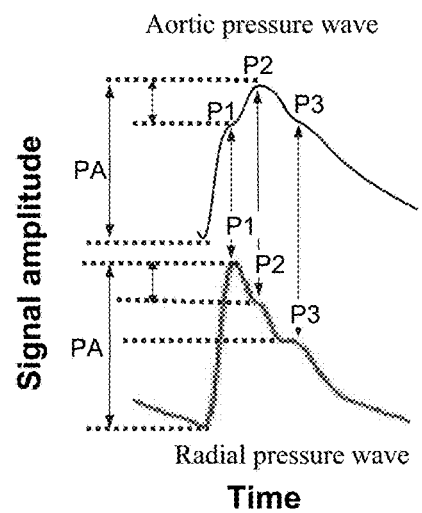
FIG. 17 shows pressure-wave patterns in the aorta and radial artery, as well as amplitudes and local peaks of the pressure waves.

FIG. 17 shows examples of some parameters extracted from the pressure-wave signals (obtained by the time integration of the torso-surface acceleration signals registered by the KardiaSens sensors), including:

a. Amplitudes, areas, $1^{st}$ and $2^{nd}$ derivatives of the $1^{st}$, $2^{nd}$, and $3^{rd}$ peaks of the pressure wave (P1, P2, P3), which are produced by the reflections of the pressure waves from various parts of the arterial tree;

b. Time lengths and time intervals between the $1^{st}$, $2^{nd}$, and $3^{rd}$ peaks of the pressure wave (P1, P2, P3);

c. The augmentation index, determined as the ratio of an absolute difference in the amplitude of the $1^{st}$ and $2^{nd}$ pressure peaks ($PA_1$ and $PA_2$, respectively) over the total amplitude of the pressure wave (PA), as shown in formula (1).

Figure 18:
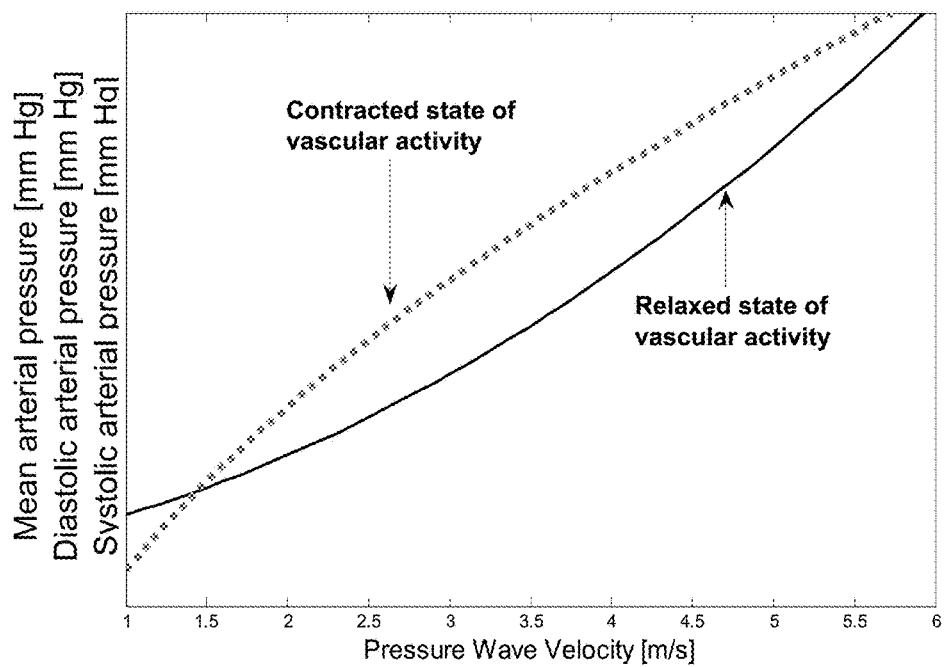
FIG. 18 is a graph of the qualitative relationship between the mean/systolic/diastolic AP and pulse-wave velocity, which has been predicted theoretically for various states of vascular activity.

FIG. 18 shows theoretically predicted shapes of relationships between the PWV and the mean/diastolic/systolic pressure for different states of vascular activity, which are elicited by different types of interventions in healthy volunteers (Roytvarf A., Shusterman V. A Large-Scale, Energetic Model of Cardiovascular Homeostasis Predicts Dynamics of Arterial Pressure in Humans. IEEE Transactions on Biomedical Engineering 2008, 55:407-418). The relaxed state of vascular activity is elicited by aerobic exercise (e.g., on a bicycle or treadmill), whereas the contracted state of vascular activity is elicited by an isometric muscle contraction during Valsalva maneuver. In particular, the experimental and theoretical study by Roytvarf and Shusterman cited above showed that a qualitatively similar relationship (to that shown in FIG. 6) exists between PWV and mean AP (MP), which is calculated as:

$$MP=(SP+2 \cdot DP)/3 \qquad (2)$$

where SP is the systolic pressure and DP is the diastolic pressure. Thus, the weight of diastolic pressure is twice that of systolic pressure, which suggests that the shapes of the relationships between PWV and MP are similar to those for PWV and DP. These theoretical predictions are shown in FIG. 18.

Figure 19A:
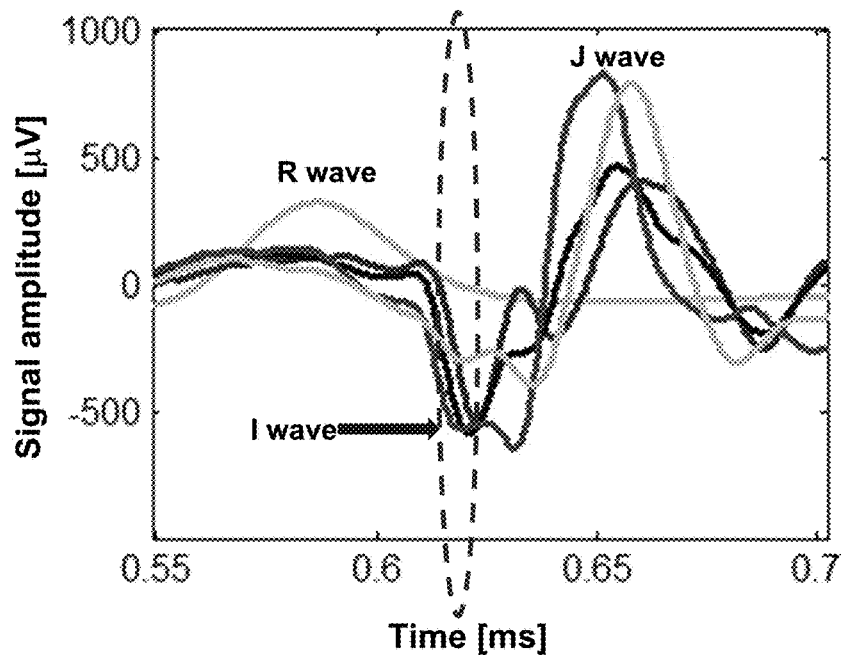
FIGS. 19A-B are selections of ECG and accelerometer signals obtained from the torso surface in a healthy subject (FIG. 19A) and in a subject with pulmonary hypertension (FIG. 19B).
Figure 19B:
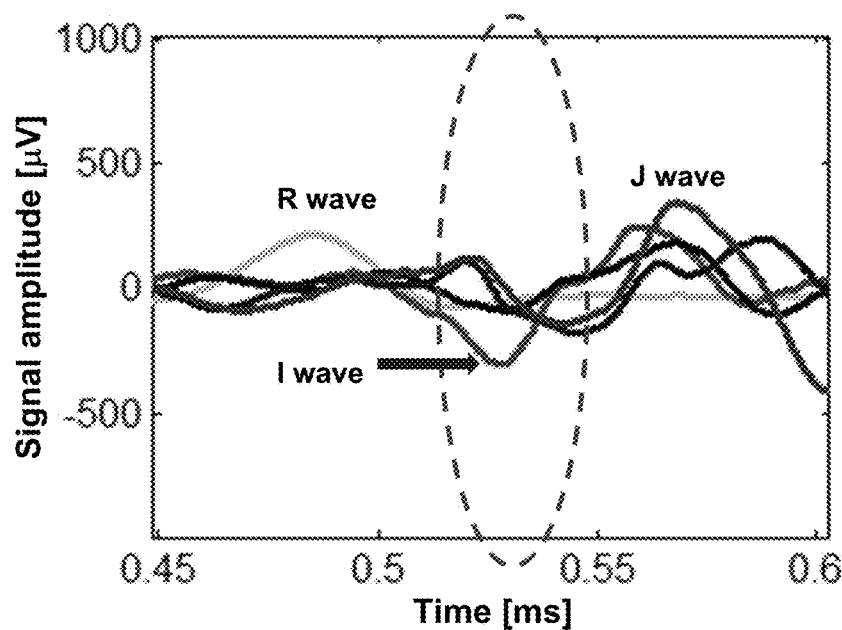

FIG. 19 shows examples of the ECG signals (lead II) and the torso-surface acceleration signals registered simultaneously by four KardiaSens sensors positioned on the torso (as shown in FIG. 14A) in a healthy subject (FIG. 19A) and a subject with pulmonary hypertension (FIG. 19B).

FIGS. 19A-B also show the ECG R wave, which may be used as a reference point for signal averaging over several cardiac cycles to improve the signal-to-noise ratio. (The ECG R wave may be also used for synchronizing the KardiaSens signals obtained non-simultaneously, over different cardiac cycles, by placing the KardiaSens sensors at various locations on the body [e.g., torso] surface.) FIG. 19 also shows examples of I and J waves/peaks in the KardiaSens data. The times and/or amplitudes of the peaks I and/or J may be used by the system of this invention for assessing the distribution of cardiac forces on the torso and/or for tracking/assessing arterial blood pressure in the central arteries. In particular, the time of occurrence of the peak I and/or J registered by KardiaSens sensors positioned at different locations (i.e., at different distances from the heart), the relative delays between the peaks registered at different locations, and/or the amplitudes of the peaks may be used by the system of this invention for tracking distributions of cardiac forces on the torso and/or the passage of AP waves in the central arteries. The dashed oval marks the area around the peak of the I wave of the torso-surface acceleration waveforms registered by the KardiaSens sensors.

The tight grouping of the peaks of the I waves registered at different torso locations by the KardiaSens sensors in FIG. 19A (as well as the sharp and narrow waveforms and clearly discernible peak amplitudes of the I and J waves) indicates synchronous, spatially homogeneous distribution of the cardiac contraction forces on the torso. By contrast, the wider distribution of the I peaks registered at different torso locations by the KardiaSens sensors in FIG. 19B (as well as the wider waveforms and lower peak amplitudes of the I and J waves) indicates asynchronous, spatially heterogeneous distribution of the cardiac contraction forces on the torso.

Figures 20A, 20B:
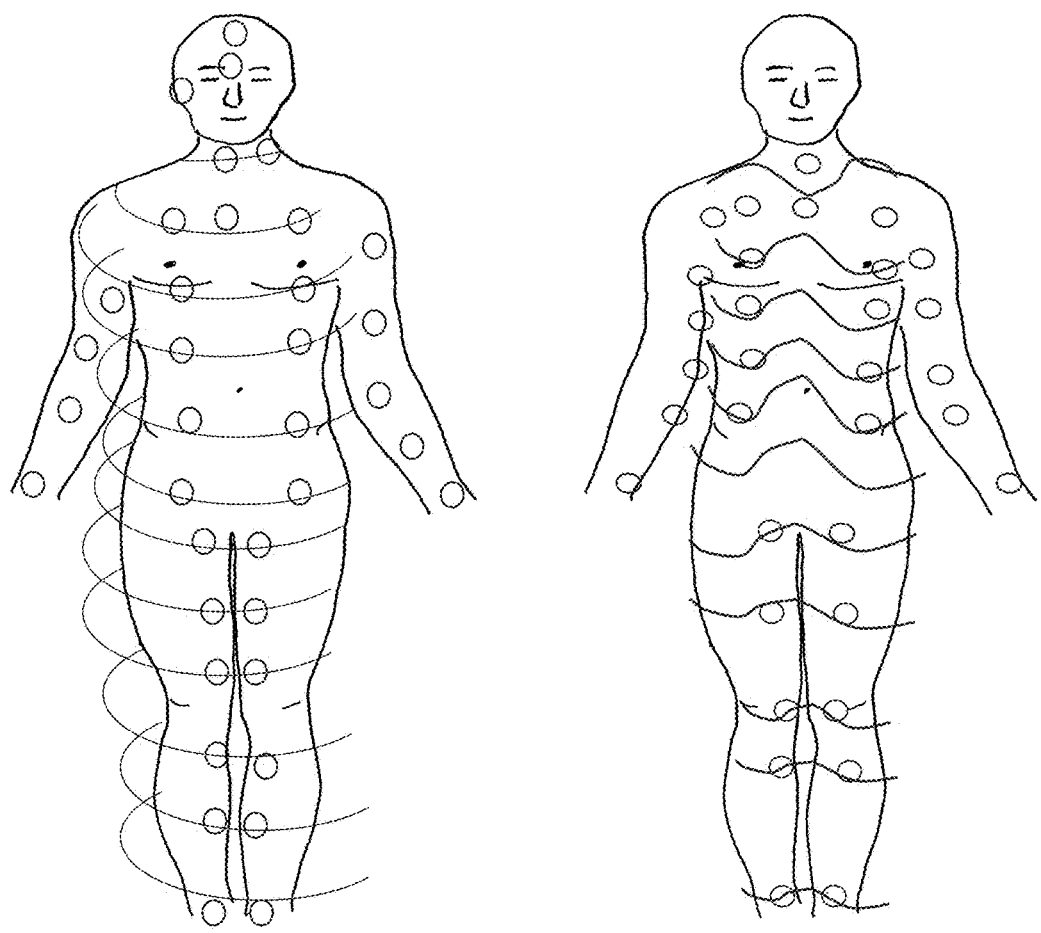
FIGS. 20A-B are examples of sensor locations for tracking body-surface accelerations associated with cardiac forces and AP waves.

FIG. 20A shows a theoretically predicted spatial distribution of the cardiac forces and/or pressure-wave characteristics (e.g., pressure-wave arrival times, amplitudes, $1^{st}$, $2^{nd}$ and $3^{rd}$ peak amplitude and durations) in the central arteries, which corresponds to the synchronous cardiac forces in FIG. 19A. Such a regular, uniform distribution is expected in individuals with normal cardiac function.

FIG. 20B shows a theoretically predicted spatial distribution of the cardiac forces and/or pressure-wave characteristics in the central arteries, which corresponds to the asynchronous cardiac forces in FIG. 19B. Such an irregular, heterogeneous (non-uniform) distribution is expected in individuals with abnormal cardiac function (e.g., left-sided and/or right-sided HF, pulmonary hypertension, asynchronous cardiac contractions).

Abnormalities in the vascular tree (e.g., aneurisms, atherosclerotic plaque, stenosis, and/or other hereditary or acquired abnormalities and malformations) may also cause or enhance irregularities of the cardiac forces and/or AP-wave characteristics (e.g., pressure-wave arrival times, amplitudes, $1^{st}$, $2^{nd}$, and $3^{rd}$ peak amplitude and durations) as shown in FIG. 19B.

The methods, systems, sensors, and devices of this invention provide the tools for extending currently available methods for the ECG body-surface mapping (and ECG imaging) to enable mapping of cardiac mechanical and electromechanical activity. Combining the spatial distributions (maps) of the cardiac (cardiovascular) mechanical activity shown in FIGS. 20A-B with ECG body-surface mapping provides a practical solution for obtaining the combined body-surface maps of cardiac or cardiovascular mechanical activity and/or electromechanical activity. Moreover, combining these measurements with the cardiac anatomy obtained, for example, from cardiac CT or MRI provides a solution for reconstructing the mechanical and/or electromechanical activity on the surface of the heart and major cardiac vessels. Obtaining such electromechanical maps in patients with cardiovascular diseases, including patients with heart failure, pulmonary hypertension, and cardiac arrhythmias, may reveal specific characteristics (e.g., location, timing, magnitude) of impaired, delayed, or desynchronized areas of cardiac mechanical activity (forces). This information may be useful for improved diagnosis of cardiovascular diseases and their efficient management.

We note that the methods, systems, sensors, and devices of this invention provide the tools for registering, constructing, and analyzing the spatiotemporal (space-time) distributions of the cardiac mechanical forces on the surface of the torso. The patterns of those distributions, including their regularity/irregularity, location of the extrema (maxima and/or minima), directions, isochronal maps (e.g., the time of occurrence of the I and/or J peaks registered by the Kardia-Sens sensors at different torso locations) may be useful for:
  a. The diagnosis of the type of HF (e.g., left-sided or right-sided);
  b. Tracking the dynamics of the cardiac mechanical (pumping) activity in patients with chronic cardiovascular diseases (e.g., HF);
  c. Evaluating the effects of pharmacological and/or non-pharmacological treatment on cardiac mechanical activity;
  d. Evaluating the level of cardiac fitness, response to exercise, stress test, and/or other diagnostic tests, including response to one or more pharmacological agents (e.g., beta-blockers, calcium blockers, and/or vasorelaxants).

Examples of the processing steps performed by the systems, sensors, and devices of this invention include:
  determining one or more parameters of cardiovascular activity in one or more signals selected from:
    a. One or more ECG signals;
    b. One or more BCG signals;
    c. One or more accelerations of the torso surface registered by said one or more modular sensors containing one or more accelerometers;
    d. One or more pressure-wave signals; and
    e. One or more jerks of the pressure wave registered by said one or more modular cardiovascular sensors containing one or more accelerometers;
  wherein said one or more parameters of cardiovascular activity are selected from:
    a. One or more amplitudes of one or more specific peaks;
    b. One or more areas of one or more specific peaks;
    c. One or more durations of one or more specific peaks;
    d. One or more times of occurrence of one or more specific peaks;
    e. One or more statistical parameters selected from: the median, mode, standard deviation, variance, and range of temporal variation of said one or more parameters of cardiovascular activity;
    f. One or more statistical parameters selected from: the median, mode, standard deviation, variance, and range of spatial variation of said one or more parameters of cardiovascular activity in two or more sensor locations;
    g. One or more time points of the fiducial points selected from the times of occurrence of: the peak of the ECG R, P, Q, S, T, and U wave; the beginning, peak, and end of the pressure wave; the beginning, peak, and end of the pressure-wave acceleration; and the beginning, peak, and end of the pressure-wave jerk;
    h. One or more time intervals between two or more specific peaks in said one or more signals;
    i. One or more time intervals between the time of occurrence of one or more specific peaks in two or more said signals;
    j. One or more PWVs;
    k. One or more AP-wave (pulse) transit times;
    l. One or more systolic pressures;
    m. One or more diastolic pressures;
    n. One or more mean arterial pressures;
    o. One or more heart rates;
    p. One or more time intervals between cardiac beats (beat-to-beat intervals);
    q. One or more vascular properties;
    r. One or more augmentation indices;
    s. One or more electrical activation times;
    t. One or more mechanical activation times;
    u. One or more electrical repolarization times;
    v. One or more electromechanical activation times; and
    w. One or more electromechanical repolarization times;
  constructing one or more maps of cardiovascular activity using said one or more parameters of cardiovascular activity determined in said one or more signals, wherein said one or more maps are selected from the cardiac mechanical activity on the body surface, cardiac electromechanical activity on the body surface, cardiac mechanical activity on the surface of the heart, and cardiac electromechanical activity on the surface of the heart; and
  determining one or more features of said one or more maps, wherein said features are selected from:
    a. One or more anatomical locations of one or more extrema (regions of extreme [maximum and/or minimum] values);
    b. The area size of one or more extrema;
    c. The number of occurrences of extreme values;
    d. One or more anatomical locations of the maximum value;
    e. One or more anatomical locations of the minimum value;
    f. One or more differences between the times of occurrence of said one or more parameters of cardiovascular activity in two or more anatomical (sensor) locations;
    g. One or more differences between the values of said one or more parameters of cardiovascular activity in two or more anatomical (sensor) locations;
    h. One or more isochrones connecting points of simultaneous occurrence of said one or more parameters in two or more anatomical (sensor) locations.
    i. One or more contour lines connecting points of equal value respecting said one or more parameters of cardiovascular activity in two or more anatomical (sensor) locations;
    j. Smoothness of one or more parameters of said one or more maps selected from said one or more isochrones (isochronal lines) and contour lines; and
    k. Curvature of one or more parameters of said one or more maps selected from said one or more isochrones and contour lines;

calibrating said one or more parameters of cardiovascular mechanical activity with respect to one or more reference values selected from:
  a. One or more systolic pressures;
  b. One or more diastolic pressures;
  c. One or more mean APs;
  d. One or more heart rates;
  e. One or more time intervals between cardiac beats (beat-to-beat cardiac intervals);
  f. One or more vascular properties;
  g. One or more AP-wave (pulse) transit times;
  h. One or more AP-wave velocities;
  i. One or more individual's baseline values;
  j. One or more characteristics of displacement from baseline values;
  k. One or more magnitudes, ranges, speeds, time lengths, and patterns of temporal changes;
  l. One or more magnitudes, ranges, speeds, time lengths, and patterns of spatial changes with respect to one or more anatomical locations;
  m. One or more augmentation indices;
  n. One or more functional relationships between two or more reference values;
  o. One or more measures of similarity with an individual's baseline (typical) values;
  p. One or more measures of difference with an individual's baseline values;
  q. One or more measures of similarity with one or more typical patterns for an individual;
  r. One or more measures of similarity with one or more baseline values in a group of subjects;
  s. One or more measures of difference with group baseline values in a group of subjects;
  t. One or more measures of similarity with one or more typical patterns for a group of subjects;
  u. One or more functional relationships between said one or more parameters and two or more reference points within one or more reference signals selected from:
    A. Systolic pressure;
    B. Diastolic pressure;
    C. Mean AP;
    D. Heart rate;
    E. AP-wave (pulse) transit time;
    F. AP-wave velocity;
    G. One or more vascular properties;
    H. One or more functional relationships between said one or more parameters and two or more reference points in two or more said reference signals;
computing one or more indicators of synchrony between cardiovascular activity in two or more cardiac regions (segments) using said one or more parameters of cardiovascular activity (e.g., electrophysiological [electrical] activation times, electrical repolarization [recovery] times, mechanical activation times, mechanical recovery times, patterns of electrical excitation [depolarization], patterns of electrical repolarization, and patterns of mechanical activation), wherein said two or more cardiac regions are selected from the left ventricle; right ventricle; left atrium; right atrium; apex; base; the anterior, posterior, lateral, and inferior walls of the left ventricle; interventricular septum; the anterior, inferior, and lateral (free) wall of the right ventricle; and the left ventricular and right ventricular segments selected from basal, mid, and apical segments;

identifying one or more segments (regions) of the heart that do not contract (i.e., do not contribute to the mechanical contraction of the heart), and excluding measurements from those regions from the assessment of synchrony, wherein said one or more regions of the heart that do not contract are identified using one or more data types selected from imaging data (MRI data, CT imaging data, ultrasound imaging), ECG data, and cardiac mechanical activity data (which may be obtained using the sensors and/or systems of this invention);
computing one or more histograms respecting statistical distribution of data with respect to one or more indicators of cardiovascular activity (e.g., electrical activation time, electrical repolarization time, mechanical activation time) for two or more cardiac regions and computing one or more indicators of synchrony between said two or more cardiac regions using a percentage (proportion, relative quantity) of said histogram data that exceed (occur after) a reference time threshold, wherein said reference time threshold is selected from:
  a. One or more constant values;
  b. One or more values respecting population (group) statistical data from one or more cardiac regions;
  c. One or more reference values respecting an individual's data from one or more cardiac regions;
adjusting one or more indicators of synchrony between cardiovascular activity in said two or more cardiac regions (segments) by weighting an expected contribution of each cardiac region to a mechanical contraction (function) of the heart to obtain a weighted assessment of synchrony in said two or more regions of the heart;
computing one or more differences between said one or more parameters of cardiovascular activity in said two or more cardiac regions;
computing one or more indicators of delayed cardiovascular activity (e.g., late electrical activation, late electrical repolarization, and/or late mechanical activation) in one or more regions of the heart, using said one or more parameters of cardiovascular activity (e.g., electrical activation time, electrical repolarization time, or mechanical activation time) to identify said cardiovascular activity that occurs after the reference time threshold, wherein said reference time threshold is selected from:
  a. One or more constant values;
  b. One or more values respecting population (group) statistical data from one or more cardiac regions;
  c. One or more reference values respecting an individual's data from one or more cardiac regions;
adjusting one or more indicators of delayed cardiovascular activity (e.g., late electrical activation, late electrical repolarization, and/or late mechanical activation) using the number of anatomical locations in which said indicators exceed the reference time threshold, wherein said reference time threshold is selected from:
  a. One or more constant values;
  b. One or more values respecting population (group) statistical data from one or more cardiac regions;
  c. One or more reference values respecting an individual's data from one or more cardiac regions;
displaying one or more indicators of synchrony of cardiovascular activity (e.g., electrical activation, electrical recovery, or mechanical activation) in two or more cardiac regions, wherein said one or more indicators are selected from a graphical indicator, numerical indicator, alphanumerical indicator, and combinations thereof for two or more regions of the heart.

Nothing in the above and attached descriptions is meant to limit the present invention to any specific materials, geometry, or orientation of elements. Many modifications are contemplated within the scope of the present invention and will be apparent to those skilled in the art. The embodiments disclosed herein were presented by way of example only and should not be used to limit the scope of the invention.

Whereas particular aspects of the method, system, sensors, and devices of the present invention and particular embodiments of the invention have been described for purposes of illustration, it will be appreciated by those skilled in the art that numerous variations of the details may be made without departing from the invention as described in the appended claims.

The invention claimed is:

1. A modular cardiovascular sensor arrangement adapted for placement on the surface of an individual's torso for monitoring at least one physiological indicator selected from cardiac mechanical activity, blood pressure, cardiac output, pulse wave velocity, and vascular activity, wherein said sensor arrangement is adapted to enable data acquisition from at least two locations on the surface of said torso, said sensor arrangement comprising:
   at least one electronic component containing at least one accelerometer, wherein said electronic component is adapted for registering torso-surface movement related to the dynamics of cardiovascular mechanical activity with resolution required to identify at least one feature of said movement over multiple cardiac cycles, and to generate at least one signal related to said cardiovascular activity registered in at least two locations on the surface of said torso;
   at least one electronic-coupling element for connecting said at least one electronic component and at least one processing module to enable sending said signal registered by said electronic component to said processing module; and
   at least one housing for said at least one electronic component which is adapted to conform to the shape of the torso surface.

2. A modular sensor as set forth in claim 1 which further includes a locking mechanism for securing said at least one electronic component in said housing selected from an adhesive material, connector, latch, and sheath.

3. A modular sensor as set forth in claim 2 which is adapted for exchanging at least one interchangeable component selected from an accelerometer-containing electronic component, an ECG-sensor component, an EMG-sensor component, a transthoracic-electrical-impedance component, an acoustic-sensor component, a photoplethysmographic-sensor component, a temperature-sensor component, a GSR-sensor component, an ultrasound-sensor component, a pressure-sensor component, a blood-pressure-sensor component, a heart-rate-sensor component, a piezoelectric-sensor component, a conformal-membrane component, and a housing component, using said locking mechanism for disconnecting said at least one interchangeable component from said modular sensor and connecting another said interchangeable component to said modular sensor.

4. A modular sensor as set forth in claim 1 in which said electronic-coupling element includes at least one component selected from an electrical wire, electrical cable, electrical connector, and electronic circuitry.

5. A modular sensor as set forth in claim 1 which further includes at least one additional sensor component selected from an ECG-sensor component, an EMG-sensor component, a transthoracic-electrical-impedance-sensor component, an acoustic-sensor component, a photoplethysmographic-sensor component, a temperature-sensor component, a GSR-sensor component, an ultrasound-sensor component, a pressure-sensor component, a blood-pressure-sensor component, a heart-rate-sensor component, and a piezoelectric-sensor component.

6. A modular sensor as set forth in claim 1 in which said at least one housing is adapted to fit in at least one intercostal space of said torso.

7. A modular sensor as set forth in claim 1 in which said at least one housing is incorporated into at least one arrangement selected from clothing, a conformal patch, body strap, conformal strap, band, belt, vest, conformal vest, and portable device.

8. A modular sensor as set forth in claim 1 in which said at least one housing uses at least one conformal material.

9. A modular sensor as set forth in claim 1 in which said housing further includes at least one conformal membrane, which is adapted for providing contact with an individual's skin surface on one side of the membrane and with said at least one electronic component on the other side of said membrane.

10. A process for manufacturing a modular cardiovascular sensor, wherein said sensor is adapted for placement on the surface of an individual's body to determine, substantially simultaneously, at least one parameter of cardiovascular activity in at least two locations of the body, said process comprising:
    providing at least one electronic component containing an accelerometer, wherein said electronic component is adapted for registering body surface movement related to cardiovascular mechanical activity and has at least one electronic-coupling element to provide connection between said at least one electronic component and at least one external electronic device;
    providing at least one housing adapted to conform to the shape of the body surface and said electronic component, said housing further comprising at least one membrane, which is adapted for providing contact with an individual's skin surface on one side of said membrane and with said electronic component on the other side of said membrane.

11. A process for manufacturing modular sensors as set forth in claim 10 in which at least one locking mechanism for connecting said at least one electronic component to said at least one housing is selected from at least one connector, latch, sheath, wire, soldered connection, and solder joint.

12. A process for manufacturing modular sensors as set forth in claim 10 in which said at least one housing uses at least one conformal material.

13. A system for dynamical evaluation of at least one indicator selected from cardiovascular mechanical activity, arterial blood pressure, cardiac output, and vascular properties, said system comprising:
    at least one modular cardiovascular sensor containing at least one accelerometer, wherein said sensor is adapted for placement on an individual's body for registering signals related to body surface movement respecting cardiovascular mechanical activity;
    an acquisition module for acquiring information from said at least one sensor; and a processing module for processing said information from said at least one sensor, wherein said processing module is adapted to determine at least one parameter of cardiovascular activity substantially simultaneously in at least two locations on the body surface and is further adapted to map the cardiovascular mechanical activity using said at least one parameter obtained from said at least two locations on said body.

14. A system as set forth in claim 13, which is further configured to provide information useful for at least one evaluation selected from: evaluation of the cardiovascular mechanical activity, evaluation of asynchrony of the cardiac mechanical activity, evaluation of heart-failure status, evaluation of pulmonary-hypertension status, evaluation of central arterial pressure, evaluation of blood pressure, evaluation of sleep-disordered breathing, including apnea and hypopnea, evaluation of cardiovascular fitness, evaluation of the stress test, evaluation of the exercise test, and evaluation of at least one effect of a pharmacologic agent.

15. A system as set forth in claim 13 in which said at least one sensor is incorporated into at least one arrangement selected from clothing, a conformal patch, body strap, conformal strap, belt, band, vest, conformal vest, and portable device.

16. A system as set forth in claim 13 in which said at least one modular cardiovascular sensor is enclosed in at least one conformal housing.

17. A system as set forth in claim 13, in which said processing module performs at least one of the following processing steps:
   determining at least one parameter of cardiovascular activity in at least one signal selected from:
   A) At least one ECG signal;
   B) At least one BCG signal;
   C) At least one acceleration of the body surface registered by said at least one modular sensor containing at least one accelerometer;
   D) At least one pressure-wave signal; and
   E) At least one jerk of the pressure wave registered by said at least one modular cardiovascular sensor containing at least one accelerometer;
   wherein said at least one parameter of cardiovascular activity is selected from:
   a) At least one amplitude of at least one specific peak;
   b) At least one area of at least one specific peak;
   c) At least one duration of at least one specific peak;
   d) At least one time of occurrence of at least one specific peak;
   e) At least one statistical parameter selected from: the median, mode, standard deviation, variance, and range of temporal variation of said at least one parameter of cardiovascular activity;
   f) At least one statistical parameter selected from: the median, mode, standard deviation, variance, and range of spatial variation of said at least one parameter of cardiovascular activity in at least two sensor locations;
   g) At least one time point of the fiducial points selected from the times of occurrence of: the peak of the ECG R, P, Q, S, T, and U wave; the beginning, peak, and end of the pressure wave; the beginning, peak, and end of the pressure-wave acceleration; and the beginning, peak, and end of the pressure-wave jerk;
   h) At least one time interval between at least two specific peaks in at least one said signal;
   i) At least one time interval between the time of occurrence of at least one specific peak in at least two said signals;
   j) At least one PWV (pulse wave velocity);
   k) At least one AP-wave (pulse) transit time;
   l) At least one systolic pressure;
   m) At least one diastolic pressure;
   n) At least one mean arterial pressure;
   o) At least one heart rate;
   p) At least one time interval between cardiac beats (beat-to-beat interval);
   q) At least one vascular property;
   r) At least one augmentation index;
   s) At least one electrical activation time;
   t) At least one mechanical activation time;
   u) At least one electrical repolarization time;
   v) At least one electromechanical activation time; and
   w) At least one electromechanical repolarization time;
   constructing at least one map of cardiovascular activity using said at least one parameter of cardiovascular activity determined in at least one said signal, wherein said at least one map is selected from the cardiac mechanical activity on the body surface, cardiac electromechanical activity on the body surface, cardiac mechanical activity on the surface of the heart, and cardiac electromechanical activity on the surface of the heart; and
   determining at least one feature of said at least one map, wherein said feature is selected from:
   A) At least one anatomical location of at least one extremum;
   B) At least one size of at least one extremum;
   C) At least one number of occurrences of extreme values;
   D) At least one anatomical location of the maximum value;
   E) At least one anatomical location of the minimum value;
   F) At least one difference between the times of occurrence of said at least one parameter of cardiovascular activity in at least two anatomical locations;
   G) At least one difference between the values of said at least one parameter of cardiovascular activity in at least two anatomical locations;
   H) At least one isochrone connecting points of simultaneous occurrence of said at least one parameter in at least two anatomical locations;
   I) At least one contour line connecting points of equal value respecting said at least one parameter of cardiovascular activity in at least two anatomical locations;
   J) Smoothness of at least one parameter of said at least one map selected from said at least one isochrone and said at least one contour line; and
   K) Curvature of at least one parameter of said at least one map selected from said at least one isochrone and said at least one contour line;
   calibrating said at least one parameter of cardiovascular activity with respect to at least one reference value selected from:
   A) At least one systolic pressure;
   B) At least one diastolic pressure;
   C) At least one mean AP;
   D) At least one heart rate;
   E) At least one time interval between cardiac beats (beat-to-beat cardiac interval);
   F) At least one vascular property;
   G) At least one AP-wave (pulse) transit time;
   H) At least one AP-wave velocity;
   I) At least one individual's baseline value;

J) At least one characteristic of displacement from baseline values;
K) At least one parameter selected from the magnitude, range, speed, time length, and pattern of temporal changes;
L) At least one parameter selected from the magnitude, range, speed, time length, and pattern of spatial changes with respect to at least one anatomical location;
M) At least one augmentation index;
N) At least one functional relationship between at least two reference values;
O) At least one measure of similarity with an individual's baseline (typical) values;
P) At least one measure of difference with an individual's baseline values;
Q) At least one measure of similarity with at least one typical pattern for an individual;
R) At least one measure of similarity with at least one baseline value in a group of subjects;
S) At least one measure of difference with at least one baseline value for a group of subjects;
T) At least one measure of similarity with at least one typical pattern for a group of subjects;
U) At least one functional relationship between said at least one parameter of cardiovascular activity and at least two reference points within at least one reference signal selected from:
  a) Systolic pressure;
  b) Diastolic pressure;
  c) Mean AP;
  d) Heart rate;
  e) AP-wave (pulse) transit time;
  f) AP-wave velocity;
  g) At least one vascular property;
  h) At least one functional relationship between said at least one parameter of cardiovascular activity and at least two reference points in at least two said reference signals;
computing at least one indicator of synchrony between cardiovascular activity in at least two cardiac regions using said at least one parameter of cardiovascular activity selected from: electrical activation times, electrical recovery times, mechanical activation times, mechanical recovery times, patterns of electrical excitation, patterns of electrical repolarization, and patterns of mechanical activation, wherein said at least two cardiac regions are selected from the left ventricle; right ventricle; left atrium; right atrium; apex; base; the anterior, posterior, lateral, and inferior walls of the left ventricle; interventricular septum; the anterior, inferior, and lateral (free) wall of the right ventricle; and the left ventricular and right ventricular segments selected from basal, mid, and apical segments;
identifying at least one region of the heart that does not contract and excluding measurements from that region from the assessment of synchrony, wherein said at least one region of the heart that does not contract is identified using at least one data type selected from MRI data, CT imaging data, ultrasound imaging data, ECG data, and cardiac mechanical activity data;
computing at least one histogram respecting statistical distribution of data with respect to at least one indicator of cardiovascular activity selected from electrical activation time, electrical repolarization time, and mechanical activation time for at least two cardiac regions, and computing at least one indicator of synchrony between said at least two cardiac regions using a proportion of said histogram data that exceeds a reference time threshold, wherein said reference time threshold is selected from:
A) At least one constant value;
B) At least one value respecting population (group) statistical data from at least one cardiac region;
C) At least one reference value respecting an individual's data from at least one cardiac region;
  adjusting at least one indicator of synchrony between cardiovascular activity in said at least two cardiac regions by weighting an expected contribution of each cardiac region to a mechanical contraction of the heart to obtain a weighted assessment of synchrony in said at least two regions of the heart;
  computing at least one difference between said at least one parameter of cardiovascular activity in said at least two cardiac regions;
  computing at least one indicator of delayed cardiovascular activity selected from delayed electrical activation, delayed electrical repolarization, and delayed mechanical activation in at least one region of the heart, using said at least one parameter of cardiovascular activity to identify said cardiovascular activity that occurs after the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  adjusting at least one indicator of delayed cardiovascular activity selected from delayed electrical activation, delayed electrical repolarization, and delayed mechanical activation, using the number of anatomical locations in which said at least one indicator exceeds the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  displaying at least one indicator of synchrony of cardiovascular activity selected from electrical activation, electrical recovery, and mechanical activation in at least two cardiac regions, wherein said at least one indicator is selected from a graphical indicator, numerical indicator, alphanumerical indicator, and combinations thereof for at least two regions of the heart.

18. A portable device for monitoring at least one physiological indicator selected from cardiovascular mechanical activity, arterial blood pressure, cardiac output, and vascular activity, said device comprising:
  at least one sensor which is adapted for placement on the surface of an individual's body and which contains at least one accelerometer for measuring body surface movement related to cardiovascular mechanical activity;
  at least one acquisition module for acquiring information from said at least one sensor over multiple cardiac cycles;

at least one module selected from a communication module and a data-storage module for transferring said information to an external processing module, wherein said processing module is adapted to determine at least one parameter of cardiovascular activity substantially simultaneously in at least two locations on the body surface and is further adapted to map the cardiovascular mechanical activity using said at least one parameter obtained from said at least two locations.

19. A device as set forth in claim 18, which is further configured to provide information useful for at least one evaluation selected from: evaluation of the cardiovascular mechanical activity, evaluation of asynchrony of the cardiac mechanical activity, evaluation of heart-failure status, evaluation of pulmonary-hypertension status, evaluation of central arterial pressure, evaluation of blood pressure, evaluation of sleep-disordered breathing, including apnea and hypopnea, evaluation of cardiovascular fitness, evaluation of the stress test, evaluation of the exercise test, and evaluation of at least one effect of a pharmacologic agent.

20. A device as set forth in claim 18 in which said at least one sensor is incorporated into at least one conformal arrangement selected from clothing, a conformal patch, body strap, conformal strap, belt, band, vest, conformal vest, and portable device.

21. A device as set forth in claim 18 in which said at least one modular cardiovascular sensor is enclosed in at least one conformal housing.

22. A device as set forth in claim 18 in which said processing module performs at least one of the following processing steps:
  determining at least one parameter of cardiovascular activity in at least one signal selected from:
  A) At least one ECG signal;
  B) At least one BCG signal;
  C) At least one acceleration of the body surface registered by said at least one modular sensor containing at least one accelerometer;
  D) At least one pressure-wave signal; and
  E) At least one jerk of the pressure wave registered by said at least one modular cardiovascular sensor containing at least one accelerometer;
  wherein said at least one parameter of cardiovascular activity is selected from:
  a) At least one amplitude of at least one specific peak;
  b) At least one area of at least one specific peak;
  c) At least one duration of at least one specific peak;
  d) At least one time of occurrence of at least one specific peak;
  e) At least one statistical parameter selected from: the median, mode, standard deviation, variance, and range of temporal variation of said at least one parameter of cardiovascular activity;
  f) At least one statistical parameter selected from: the median, mode, standard deviation, variance, and range of spatial variation of said at least one parameter of cardiovascular activity in at least two sensor locations;
  g) At least one time point of the fiducial points selected from the times of occurrence of: the peak of the ECG R, P, Q, S, T, and U wave; the beginning, peak, and end of the pressure wave; the beginning, peak, and end of the pressure-wave acceleration; and the beginning, peak, and end of the pressure-wave jerk;
  h) At least one time interval between at least two specific peaks in at least one said signal;
  i) At least one time interval between the time of occurrence of at least one specific peak in at least two said signals;
  j) At least one PWV;
  k) At least one AP-wave (pulse) transit time;
  l) At least one systolic pressure;
  m) At least one diastolic pressure;
  n) At least one mean arterial pressure;
  o) At least one heart rate;
  p) At least one time interval between cardiac beats (beat-to-beat interval);
  q) At least one vascular property;
  r) At least one augmentation index;
  s) At least one electrical activation time;
  t) At least one mechanical activation time;
  u) At least one electrical repolarization time;
  v) At least one electromechanical activation time; and
  w) At least one electromechanical repolarization time;
  constructing at least one map of cardiovascular activity using said at least one parameter of cardiovascular activity determined in at least one said signal, wherein said at least one map is selected from the cardiac mechanical activity on the body surface, cardiac electromechanical activity on the body surface, cardiac mechanical activity on the surface of the heart, and cardiac electromechanical activity on the surface of the heart; and
  determining at least one feature of said at least one map, wherein said feature is selected from:
  A) At least one anatomical location of at least one extremum;
  B) At least one size of at least one extremum;
  C) At least one number of occurrences of extreme values;
  D) At least one anatomical location of the maximum value;
  E) At least one anatomical location of the minimum value;
  F) At least one difference between the times of occurrence of said at least one parameter of cardiovascular activity in at least two anatomical locations;
  G) At least one difference between the values of said at least one parameter of cardiovascular activity in at least two anatomical locations;
  H) At least one isochrone connecting points of simultaneous occurrence of said at least one parameter in at least two anatomical locations;
    I) At least one contour line connecting points of equal value respecting said at least one parameter of cardiovascular activity in at least two anatomical locations;
  J) Smoothness of at least one parameter of said at least one map selected from said at least one isochrone and said at least one contour line; and
  K) Curvature of at least one parameter of said at least one map selected from said at least one isochrone and said at least one contour line;
  calibrating said at least one parameter of cardiovascular activity with respect to at least one reference value selected from:
  A) At least one systolic pressure;
  B) At least one diastolic pressure;
  C) At least one mean AP;
  D) At least one heart rate;
  E) At least one time interval between cardiac beats (beat-to-beat cardiac interval);
  F) At least one vascular property;
  G) At least one AP-wave (pulse) transit time;
  H) At least one AP-wave velocity;

I) At least one individual's baseline value;
J) At least one characteristic of displacement from baseline values;
K) At least one parameter selected from the magnitude, range, speed, time length, and pattern of temporal changes;
L) At least one parameter selected from the magnitude, range, speed, time length, and pattern of spatial changes with respect to at least one anatomical location;
M) At least one augmentation index;
N) At least one functional relationship between at least two reference values;
O) At least one measure of similarity with an individual's baseline (typical) values;
P) At least one measure of difference with an individual's baseline values;
Q) At least one measure of similarity with at least one typical pattern for an individual;
R) At least one measure of similarity with at least one baseline value in a group of subjects;
S) At least one measure of difference with at least one baseline value for a group of subjects;
T) At least one measure of similarity with at least one typical pattern for a group of subjects;
U) At least one functional relationship between said at least one parameter of cardiovascular activity and at least two reference points within at least one reference signal selected from:
  a) Systolic pressure;
  b) Diastolic pressure;
  c) Mean AP;
  d) Heart rate;
  e) AP-wave (pulse) transit time;
  f) AP-wave velocity;
  g) At least one vascular property;
  h) At least one functional relationship between said at least one parameter of cardiovascular activity and at least two reference points in at least two said reference signals;
computing at least one indicator of synchrony between cardiovascular activity in at least two cardiac regions using said at least one parameter of cardiovascular activity selected from: electrical activation times, electrical recovery times, mechanical activation times, mechanical recovery times, patterns of electrical excitation, patterns of electrical repolarization, and patterns of mechanical activation, wherein said at least two cardiac regions are selected from the left ventricle; right ventricle; left atrium; right atrium; apex; base; the anterior, posterior, lateral, and inferior walls of the left ventricle; interventricular septum; the anterior, inferior, and lateral (free) wall of the right ventricle; and the left ventricular and right ventricular segments selected from basal, mid, and apical segments;
identifying at least one region of the heart that does not contract and excluding measurements from that region from the assessment of synchrony, wherein said at least one region of the heart that does not contract is identified using at least one data type selected from MRI data, CT imaging data, ultrasound imaging data, ECG data, and cardiac mechanical activity data;
computing at least one histogram respecting statistical distribution of data with respect to at least one indicator of cardiovascular activity selected from electrical activation time, electrical repolarization time, and mechanical activation time for at least two cardiac regions, and computing at least one indicator of synchrony between said at least two cardiac regions using a proportion of said histogram data that exceeds a reference time threshold, wherein said reference time threshold is selected from:
A) At least one constant value;
B) At least one value respecting population (group) statistical data from at least one cardiac region;
C) At least one reference value respecting an individual's data from at least one cardiac region;
  adjusting at least one indicator of synchrony between cardiovascular activity in said at least two cardiac regions by weighting an expected contribution of each cardiac region to a mechanical contraction of the heart to obtain a weighted assessment of synchrony in said at least two regions of the heart;
  computing at least one difference between said at least one parameter of cardiovascular activity in said at least two cardiac regions;
  computing at least one indicator of delayed cardiovascular activity selected from delayed electrical activation, delayed electrical repolarization, and delayed mechanical activation in at least one region of the heart, using said at least one parameter of cardiovascular activity to identify said cardiovascular activity that occurs after the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  adjusting at least one indicator of delayed cardiovascular activity selected from delayed electrical activation, delayed electrical repolarization, and delayed mechanical activation, using the number of anatomical locations in which said at least one indicator exceeds the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  displaying at least one indicator of synchrony of cardiovascular activity selected from electrical activation, electrical recovery, and mechanical activation in at least two cardiac regions, wherein said at least one indicator is selected from a graphical indicator, numerical indicator, alphanumerical indicator, and combinations thereof for at least two regions of the heart.

23. A system for cardiovascular electromechanical mapping, said system comprising:
at least one modular cardiovascular sensor containing at least one accelerometer and at least one ECG sensor component, wherein said modular cardiovascular sensor is adapted for placement on the surface of an individual's body for registering ECG signals and signals related to body surface movement respecting cardiovascular mechanical activity;
an acquisition module for acquiring information from said at least one modular cardiovascular sensor; and a processing module for processing said information from said at least one modular cardiovascular sensor to determine at least one parameter of cardiovascular activity in at least two locations on the body surface substantially simultaneously and is further adapted to map the cardiovascular activity using said at least one parameter obtained from said at least two locations.

24. A system as set forth in claim 23 which is configured for guiding cardiac resynchronization therapy.

25. A system as set forth in claim 23 in which said at least one modular cardiovascular sensor is incorporated into at least one conformal arrangement selected from clothing, a conformal patch, body strap, conformal strap, belt, band, vest, conformal vest, and portable device.

26. A system as set forth in claim 23 which is further configured to provide information useful for at least one evaluation selected from: evaluation of the cardiovascular mechanical activity, evaluation of asynchrony of the cardiac mechanical activity, evaluation of heart-failure status, evaluation of pulmonary-hypertension status, evaluation of central arterial pressure, evaluation of blood pressure, evaluation of sleep-disordered breathing, including apnea and hypopnea, evaluation of the cardiovascular fitness, evaluation of the stress test, evaluation of the exercise test, and evaluation of at least one effect of a pharmacologic agent.

27. A system as set forth in claim 23 in which said at least one modular cardiovascular sensor is enclosed in at least one conformal housing.

28. A system as set forth in claim 23, in which said processing module performs at least one of the following processing steps:
　determining at least one parameter of cardiovascular activity in at least one signal selected from:
　A) At least one ECG signal;
　B) At least one BCG signal;
　C) At least one acceleration of the body surface registered by said at least one modular sensor containing at least one accelerometer;
　D At least one pressure-wave signal; and
　E At least one jerk of the pressure wave registered by said at least one modular cardiovascular sensor containing at least one accelerometer;
　wherein said at least one parameter of cardiovascular activity is selected from:
　　a) At least one amplitude of at least one specific peak;
　　b) At least one area of at least one specific peak;
　　c) At least one duration of at least one specific peak;
　　d) At least one time of occurrence of at least one specific peak;
　　e) At least one statistical parameter selected from: the median, mode, standard deviation, variance, and range of temporal variation of said at least one parameter of cardiovascular activity;
　　f) At least one statistical parameter selected from: the median, mode, standard deviation, variance, and range of spatial variation of said at least one parameter of cardiovascular activity in at least two sensor locations;
　　g) At least one time point of the fiducial points selected from the times of occurrence of: the peak of the ECG R, P, Q, S, T, and U wave; the beginning, peak, and end of the pressure wave; the beginning, peak, and end of the pressure-wave acceleration; and the beginning, peak, and end of the pressure-wave jerk;
　　h) At least one time interval between at least two specific peaks in at least one said signal;
　　i) At least one time interval between the time of occurrence of at least one specific peak in at least two said signals;
　　j) At least one PWV;
　　k) At least one AP-wave (pulse) transit time;
　　l) At least one systolic pressure;
　　m) At least one diastolic pressure;
　　n) At least one mean arterial pressure;
　　o) At least one heart rate;
　　p) At least one time interval between cardiac beats (beat-to-beat interval);
　　q) At least one vascular property;
　　r) At least one augmentation index;
　　s) At least one electrical activation time;
　　t) At least one mechanical activation time;
　　u) At least one electrical repolarization time;
　　v) At least one electromechanical activation time; and
　　w) At least one electromechanical repolarization time;
　constructing at least one map of cardiovascular activity using said at least one parameter of cardiovascular activity determined in at least one said signal, wherein said at least one map is selected from the cardiac mechanical activity on the body surface, cardiac electromechanical activity on the body surface, cardiac mechanical activity on the surface of the heart, and cardiac electromechanical activity on the surface of the heart; and
　determining at least one feature of said at least one map, wherein said feature is selected from:
　A) At least one anatomical location of at least one extremum;
　B) At least one size of at least one extremum;
　C) At least one number of occurrences of extreme values;
　D) At least one anatomical location of the maximum value;
　E) At least one anatomical location of the minimum value;
　F) At least one difference between the times of occurrence of said at least one parameter of cardiovascular activity in at least two anatomical locations;
　G) At least one difference between the values of said at least one parameter of cardiovascular activity in at least two anatomical locations;
　H) At least one isochrone connecting points of simultaneous occurrence of said at least one parameter in at least two anatomical locations;
　I) At least one contour line connecting points of equal value respecting said at least one parameter of cardiovascular activity in at least two anatomical locations;
　J) Smoothness of at least one parameter of said at least one map selected from said at least one isochrone and said at least one contour line; and
　K) Curvature of at least one parameter of said at least one map selected from said at least one isochrone and said at least one contour line;
　calibrating said at least one parameter of cardiovascular activity with respect to at least one reference value selected from:
　A) At least one systolic pressure;
　B) At least one diastolic pressure;
　C) At least one mean AP;
　D) At least one heart rate;
　E) At least one time interval between cardiac beats (beat-to-beat cardiac interval);
　F) At least one vascular property;
　G) At least one AP-wave (pulse) transit time;
　H) At least one AP-wave velocity;
　I) At least one individual's baseline value;

J) At least one characteristic of displacement from baseline values;
K) At least one parameter selected from the magnitude, range, speed, time length, and pattern of temporal changes;
L) At least one parameter selected from the magnitude, range, speed, time length, and pattern of spatial changes with respect to at least one anatomical location;
M) At least one augmentation index;
N) At least one functional relationship between at least two reference values;
O) At least one measure of similarity with an individual's baseline (typical) values;
P) At least one measure of difference with an individual's baseline values;
Q) At least one measure of similarity with at least one typical pattern for an individual;
R) At least one measure of similarity with at least one baseline value in a group of subjects;
S) At least one measure of difference with at least one baseline value for a group of subjects;
T) At least one measure of similarity with at least one typical pattern for a group of subjects;
U) At least one functional relationship between said at least one parameter of cardiovascular activity and at least two reference points within at least one reference signal selected from:
  a) Systolic pressure;
  b) Diastolic pressure;
  c) Mean AP;
  d) Heart rate;
  e) AP-wave (pulse) transit time;
  f) AP-wave velocity;
  g) At least one vascular property;
  h) At least one functional relationship between said at least one parameter of cardiovascular activity and at least two reference points in at least two said reference signals;
computing at least one indicator of synchrony between cardiovascular activity in at least two cardiac regions using said at least one parameter of cardiovascular activity selected from: electrical activation times, electrical recovery times, mechanical activation times, mechanical recovery times, patterns of electrical excitation, patterns of electrical repolarization, and patterns of mechanical activation, wherein said at least two cardiac regions are selected from the left ventricle; right ventricle; left atrium; right atrium; apex; base; the anterior, posterior, lateral, and inferior walls of the left ventricle; interventricular septum; the anterior, inferior, and lateral (free) wall of the right ventricle; and the left ventricular and right ventricular segments selected from basal, mid, and apical segments;
identifying at least one region of the heart that does not contract and excluding measurements from that region from the assessment of synchrony, wherein said at least one region of the heart that does not contract is identified using at least one data type selected from MRI data, CT imaging data, ultrasound imaging data, ECG data, and cardiac mechanical activity data;
computing at least one histogram respecting statistical distribution of data with respect to at least one indicator of cardiovascular activity selected from electrical activation time, electrical repolarization time, and mechanical activation time for at least two cardiac regions, and computing at least one indicator of synchrony between said at least two cardiac regions using a proportion of said histogram data that exceeds a reference time threshold, wherein said reference time threshold is selected from:
A) At least one constant value;
B) At least one value respecting population (group) statistical data from at least one cardiac region;
C) At least one reference value respecting an individual's data from at least one cardiac region;
  adjusting at least one indicator of synchrony between cardiovascular activity in said at least two cardiac regions by weighting an expected contribution of each cardiac region to a mechanical contraction of the heart to obtain a weighted assessment of synchrony in said at least two regions of the heart;
  computing at least one difference between said at least one parameter of cardiovascular activity in said at least two cardiac regions;
  computing at least one indicator of delayed cardiovascular activity selected from delayed electrical activation, delayed electrical repolarization, and delayed mechanical activation in at least one region of the heart, using said at least one parameter of cardiovascular activity to identify said cardiovascular activity that occurs after the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  adjusting at least one indicator of delayed cardiovascular activity selected from delayed electrical activation, delayed electrical repolarization, and delayed mechanical activation, using the number of anatomical locations in which said at least one indicator exceeds the reference time threshold, wherein said reference time threshold is selected from:
A) At least one constant value;
B) At least one value respecting statistical data from at least one cardiac region for at least one group of subjects;
C) At least one reference value respecting an individual's data from at least one cardiac region;
  displaying at least one indicator of synchrony of cardiovascular activity selected from electrical activation, electrical recovery, and mechanical activation in at least two cardiac regions, wherein said at least one indicator is selected from a graphical indicator, numerical indicator, alphanumerical indicator, and combinations thereof for at least two regions of the heart.

* * * * *